United States Patent
Smith et al.

(10) Patent No.: US 7,939,021 B2
(45) Date of Patent: May 10, 2011

(54) DROPLET ACTUATOR ANALYZER WITH CARTRIDGE

(75) Inventors: Gregory F. Smith, Durham, NC (US); Ryan A. Sturmer, Durham, NC (US); Philip Y. Paik, Durham, NC (US); Vijay Srinivasan, Durham, NC (US); Michael G. Pollack, Durham, NC (US); Vamsee K. Pamula, Durham, NC (US); Keith R. Brafford, Durham, NC (US); Richard M. West, Durham, NC (US)

(73) Assignees: Advanced Liquid Logic, Inc., Research Triangle Park, NC (US); Duke University, Durham, NC (US)

( * ) Notice: Subject to any disclaimer, the term of this patent is extended or adjusted under 35 U.S.C. 154(b) by 938 days.

(21) Appl. No.: 11/838,450

(22) Filed: Aug. 14, 2007

(65) Prior Publication Data

US 2008/0281471 A1    Nov. 13, 2008

Related U.S. Application Data

(63) Continuation of application No. PCT/US2007/011298, filed on May 9, 2007.

(51) Int. Cl.
*G01N 33/00* (2006.01)
*G01N 15/06* (2006.01)
*G01N 27/00* (2006.01)
*G01N 21/00* (2006.01)
*B65D 35/00* (2006.01)
*B65D 35/28* (2006.01)
*G05B 21/00* (2006.01)

(52) U.S. Cl. ............ 422/68.1; 422/50; 422/65; 422/67; 700/266; 204/600; 222/92; 222/94; 222/95; 206/532

(58) Field of Classification Search .................. None
See application file for complete search history.

(56) References Cited

U.S. PATENT DOCUMENTS 4,390,403 A    6/1983    Batchelder
(Continued)

FOREIGN PATENT DOCUMENTS

WO    WO9822625 A1    5/1998
(Continued)

OTHER PUBLICATIONS

T.H. Zhang, K. Chakrabarty, R.B. Fair, "Behavioral modeling and performance evaluation of microelectrofluidics-based PCR systems using SystemC", IEEE Transactions on Computer-Aided Design of Integrated Circuits & Systems, vol. 23 (6): pp. 843-858, Jun. 2004.

(Continued)

*Primary Examiner* — Joseph W Drodge
*Assistant Examiner* — Jennifer Wecker
(74) *Attorney, Agent, or Firm* — William A. Barrett; Ward and Smith, P.A.

(57) ABSTRACT

A droplet actuator with cartridge is provided. According to one embodiment, a sample analyzer is provided and includes an analyzer unit comprising electronic or optical receiving means, a cartridge comprising self-contained droplet handling capabilities, and a wherein the cartridge is coupled to the analyzer unit by a means which aligns electronic and/or optical outputs from the cartridge with electronic or optical receiving means on the analyzer unit. According to another embodiment, a sample analyzer is provided and includes a sample analyzer comprising a cartridge coupled thereto and a means of electrical interface and/or optical interface between the cartridge and the analyzer, whereby electrical signals and/or optical signals may be transmitted from the cartridge to the analyzer.

35 Claims, 14 Drawing Sheets

U.S. PATENT DOCUMENTS

| | | | |
|---|---|---|---|
| 4,863,849 | A | 9/1989 | Melamede |
| 5,486,337 | A | 1/1996 | Ohkawa |
| 5,721,851 | A | 2/1998 | Cline et al. |
| 5,770,457 | A | 6/1998 | Foote et al. |
| 5,846,396 | A | 7/1998 | Stocker et al. |
| 5,851,769 | A | 12/1998 | Gray et al. |
| 5,980,719 | A | 11/1999 | Cherukuri et al. |
| 6,106,685 | A | 8/2000 | McBride et al. |
| 6,210,891 | B1 | 4/2001 | Nyren et al. |
| 6,258,568 | B1 | 7/2001 | Nyren |
| 6,294,063 | B1 | 9/2001 | Becker et al. |
| 6,319,668 | B1 | 11/2001 | Nova et al. |
| 6,379,929 | B1 | 4/2002 | Burns et al. |
| 6,432,290 | B1 | 8/2002 | Harrison et al. |
| 6,473,492 | B2 | 10/2002 | Prins |
| 6,485,913 | B1 | 11/2002 | Becker et al. |
| 6,538,823 | B2 | 3/2003 | Kroupenkine et al. |
| 6,545,815 | B2 | 4/2003 | Kroupenkine et al. |
| 6,565,727 | B1 | 5/2003 | Shenderov |
| 6,629,826 | B2 | 10/2003 | Yoon et al. |
| 6,665,127 | B2 | 12/2003 | Bao et al. |
| 6,761,962 | B2 | 7/2004 | Bentsen et al. |
| 6,773,566 | B2 | 8/2004 | Shenderov |
| 6,828,100 | B1 | 12/2004 | Ronaghi |
| 6,841,128 | B2 | 1/2005 | Kambara et al. |
| 6,896,855 | B1 | 5/2005 | Kohler et al. |
| 6,911,132 | B2 | 6/2005 | Pamula et al. |
| 6,949,176 | B2 | 9/2005 | Vacca et al. |
| 6,958,132 | B2 | 10/2005 | Chiou et al. |
| 6,960,437 | B2 | 11/2005 | Enzelberger et al. |
| 6,989,234 | B2 | 1/2006 | Kolar et al. |
| 7,078,168 | B2 | 7/2006 | Sylvan |
| 7,189,359 | B2 | 3/2007 | Yuan et al. |
| 7,189,560 | B2 | 3/2007 | Kim et al. |
| 7,759,132 | B2 * | 7/2010 | Pollack et al. ............... 436/180 |
| 2002/0043463 | A1 | 4/2002 | Shenderov |
| 2002/0058332 | A1 | 5/2002 | Quake et al. |
| 2002/0093651 | A1 | 7/2002 | Roe |
| 2002/0128546 | A1 | 9/2002 | Silver |
| 2002/0168671 | A1 | 11/2002 | Burns et al. |
| 2002/0172969 | A1 | 11/2002 | Burns et al. |
| 2003/0006140 | A1 | 1/2003 | Vacca et al. |
| 2003/0012483 | A1 | 1/2003 | Ticknor et al. |
| 2003/0012699 | A1 | 1/2003 | Moore et al. |
| 2003/0082081 | A1 | 5/2003 | Fouillet et al. |
| 2003/0103021 | A1 | 6/2003 | Young et al. |
| 2003/0119057 | A1 | 6/2003 | Gascoyne et al. |
| 2003/0164295 | A1 | 9/2003 | Sterling |
| 2003/0183525 | A1 | 10/2003 | Elrod et al. |
| 2003/0205632 | A1 | 11/2003 | Kim et al. |
| 2003/0206351 | A1 | 11/2003 | Kroupenkine |
| 2003/0224528 | A1 | 12/2003 | Chiou et al. |
| 2003/0227100 | A1 | 12/2003 | Chandross et al. |
| 2004/0007377 | A1 | 1/2004 | Fouillet et al. |
| 2004/0031688 | A1 | 2/2004 | Shenderov |
| 2004/0042721 | A1 | 3/2004 | Kroupenkine et al. |
| 2004/0055536 | A1 | 3/2004 | Kolar et al. |
| 2004/0055891 | A1 | 3/2004 | Pamula et al. |
| 2004/0058450 | A1 | 3/2004 | Pamula et al. |
| 2004/0091392 | A1 | 5/2004 | McBride et al. |
| 2004/0136876 | A1 | 7/2004 | Fouillet et al. |
| 2004/0141884 | A1 | 7/2004 | Unno et al. |
| 2004/0189311 | A1 * | 9/2004 | Glezer et al. ................. 324/444 |
| 2004/0231987 | A1 * | 11/2004 | Sterling et al. ................ 204/450 |
| 2004/0260204 | A1 * | 12/2004 | Boecker et al. ............... 600/584 |
| 2005/0048581 | A1 | 3/2005 | Chiu et al. |
| 2005/0056569 | A1 | 3/2005 | Yuan et al. |
| 2005/0064423 | A1 | 3/2005 | Higuchi et al. |
| 2005/0100675 | A1 | 5/2005 | Mao et al. |
| 2005/0135551 | A1 | 6/2005 | Mpock |
| 2005/0148042 | A1 | 7/2005 | Prestwich et al. |
| 2005/0158755 | A1 | 7/2005 | Lee et al. |
| 2005/0179746 | A1 | 8/2005 | Roux et al. |
| 2005/0227264 | A1 | 10/2005 | Nobile et al. |
| 2005/0287572 | A1 | 12/2005 | Mathies et al. |
| 2006/0009705 | A1 | 1/2006 | Brown |
| 2006/0021875 | A1 | 2/2006 | Griffith et al. |
| 2006/0054503 | A1 | 3/2006 | Pamula et al. |
| 2006/0068450 | A1 | 3/2006 | Combette et al. |
| 2006/0157503 | A1 * | 7/2006 | Bublewitz et al. .............. 222/94 |
| 2006/0166261 | A1 | 7/2006 | Higuchi et al. |
| 2006/0166262 | A1 | 7/2006 | Higuchi et al. |
| 2006/0172336 | A1 | 8/2006 | Higuchi et al. |
| 2006/0210435 | A1 * | 9/2006 | Alavie et al. .................... 422/65 |
| 2006/0254933 | A1 | 11/2006 | Adachi et al. |
| 2007/0141593 | A1 | 6/2007 | Lee et al. |
| 2008/0006535 | A1 * | 1/2008 | Paik et al. ..................... 204/600 |
| 2008/0138815 | A1 | 6/2008 | Brown et al. |
| 2008/0153091 | A1 | 6/2008 | Brown et al. |
| 2008/0160525 | A1 | 7/2008 | Brown et al. |
| 2008/0169184 | A1 | 7/2008 | Brown et al. |
| 2008/0171324 | A1 | 7/2008 | Brown et al. |
| 2008/0171325 | A1 | 7/2008 | Brown et al. |
| 2008/0171326 | A1 | 7/2008 | Brown et al. |
| 2008/0171327 | A1 | 7/2008 | Brown et al. |
| 2008/0171382 | A1 | 7/2008 | Brown et al. |
| 2008/0213766 | A1 | 9/2008 | Brown et al. |
| 2009/0042319 | A1 | 2/2009 | De Guzman et al. |
| 2009/0127123 | A1 | 5/2009 | Raccurt et al. |
| 2010/0096266 | A1 | 4/2010 | Kim et al. |

FOREIGN PATENT DOCUMENTS

| | | |
|---|---|---|
| WO | WO9915876 A1 | 4/1999 |
| WO | WO9917093 A1 | 4/1999 |
| WO | WO9954730 A1 | 10/1999 |
| WO | WO03069380 A1 | 8/2003 |
| WO | WO2004027490 A1 | 4/2004 |
| WO | WO2006026351 A1 | 3/2006 |
| WO | WO2007133710 A2 | 11/2007 |

OTHER PUBLICATIONS

Jian Gong et al., "Portable digital microfluidics platform with active but disposable Lab-On-Chip," Micro Electro Mechanical Systems, 17th IEEE International Conference on (MEMS), Maastricht, Netherlands, Jan. 25-29, 2004; Piscataway, NJ, IEEE, Jan. 25, 2004, pp. 355-358.

Pollack et al., "Electrowetting-Based Actuation of Droplets for Integrated Microfluidics," Lab on a Chip (LOC), vol. 2, pp. 96-101, 2002.

H. Ren, and R. B. Fair "Micro/Nano Liter Droplet Formation and Dispensing by Capacitance Metering and Electrowetting Actuation", IEEE-NANO 2002, pp. 369-372, 2002.

Altti Torkkeli, "Droplet microfluidics on a planar surface," Doctoral Dissertation, Department of Electrical Engineering, Helsinki University of Technology (Oct. 3, 2003).

Jie Ding, "System level architectural optimization of semi-reconfigurable microfluidic system," M.S. Thesis, Duke University Dept of Electrical Engineering, 2000.

Shih-Kang Fan, "Digital Microfluidics by Cross-Reference EWOD Actuation: Principle, Device, and System," PhD Dissertation, University of California Dept. of Mechanical Engineering, 2003.

Moon, Hyejin, Ph.D., "Electrowetting-on-dielectric microfluidics: Modeling, physics, and MALDI application," University of California, Los Angeles, 2005.

Mugele et al., "Electrowetting: from basics to applications," Journal of Physics: Condensed Matter, 17, pp. R705-R774 (Jul. 2005).

Ui-Chong Yi et al., "Geometric Surface Modification of Nozzles for Complete Transfer of Liquid Drops," Mechanical and Aerospace Engineering Dept., University of California, Los Angeles (UCLA); Solid-State Sensor, Actuator and Microsystems Workshop, Hilton Head Island, South Carolina, Jun. 6-10, 2004; pp. 164-167.

T. Taniguchi et al., "Chemical reactions in microdroplets by electrostatic manipulation of droplets in liquid media," Lab on a Chip, vol. 2, No. 2, pp. 19-23 (2002).

Dewey A, Srinivasan V, Icoz E, "Visual modeling and design of microelectromechanical system transducers", Microelectronics Journal, vol. 32, pp. 373-381, Apr. 2001.

Dewey A, Srinivasan V, Icoz E, "Towards a visual modeling approach to designing micro electromechanical system transducers," Journal of Micromechanics and Microengineering, vol. 9, pp. 332-340, Dec. 1999.

R.B. Fair, A. Khlystov, T. Tailor, V. Ivanov, R.D. Evans, V. Srinivasan, V. Pamula, M.G. Pollack, P.B. Griffin, and J. Zhoud, "Chemical and Biological Applications of Digital Microfluidic Devices", IEEE Design and Test of Computers, vol. 24(1): pp. 10-24 Jan.-Feb. 2007.

R.B. Fair, A. Khlystov, V. Srinivasan, V. K. Pamula, K.N. Weaver, "Integrated chemical/biochemical sample collection, pre-concentration, and analysis on a digital microfluidic lab-on-a-chip platform," Lab-on-a-Chip: Platforms, Devices, and Applications, Conf. 5591, SPIE Optics East, Philadelphia, Oct. 25-28, 2004.

R.B. Fair, V. Srinivasan, V.K. Pamula, and K.N. Weaver, "Bead-Based and Solution-Based Assays Performed on a Digital Microfluidic Platform," Biomedical Engineering Society (BMES) Fall Meeting, Baltimore, MD, Oct. 1, 2005.

R.B. Fair, V. Srinivasan, H. Ren, P. Paik, V.K. Pamula, M.G. Pollack, "Electrowetting-based On-Chip Sample Processing for Integrated Microfluidics," IEEE Inter. Electron Devices Meeting (IEDM), pp. 32.5.1-32.5.4, 2003.

Phil Paik, Vamsee K. Pamula, and K. Chakrabarty, "Thermal effects on Droplet Transport in Digital Microfluidics with Applications to Chip Cooling Processing for Integrated Microfluidics," International Conference on Thermal, Mechanics, and Thermomechanical Phenomena in Electronic Systems (ITherm), pp. 649-654, 2004.

Phil Paik, Vamsee K. Pamula, and Richard B. Fair, "Rapid droplet mixers for digital microfluidic systems," Lab on a Chip, vol. 3, pp. 253-259, 2003.

Phil Paik, Vamsee K. Pamula, Michael G. Pollack and Richard B. Fair, "Electrowetting-based droplet mixers for microfluidic systems", Lab on a Chip (LOC), vol. 3, pp. 28-33, 2003.

Vamsee K. Pamula and Krishnendu Chakrabarty, "Cooling of integrated circuits using droplet-based microfluidics," Proc. ACM Great Lakes Symposium on VLSI, pp. 84-87, Apr. 2003.

V.K. Pamula, V. Srinivasan, H. Chakrapani, R.B. Fair, E.J. Toone, "A droplet-based lab-on-a-chip for colorimetric detection of nitroaromatic explosives," Proceedings of Micro Electro Mechanical Systems, pp. 722-725, 2005.

M. G. Pollack, P. Y. Paik, A. D. Shenderov, V. K. Pamula, F. S. Dietrich, and R. B. Fair, "Investigation of electrowetting-based microfluidics for real-time PCR applications," µTAS 2003.

Pollack et al., "Electrowetting-Based Microfluidics for High-Throughput Screening," smallTalk2001 Conference Program Abstract (Aug. 2001), p. 149, San Diego.

Hong Ren, Vijay Srinivasan, Michael G. Pollack, and Richard B. Fair, "Automated electrowetting-based droplet dispensing with good reproducibility," Proc. Micro Total Analysis Systems (mTAS), pp. 993-996, 2003.

Hong Ren, Vijay Srinivasan, and Richard B. Fair, "Design and testing of an interpolating mixing architecture for electrowetting-based droplet-on-chip chemical dilution", Transducers 2003, pp. 619-622, 2003.

Vijay Srinivasan, Vamsee K. Pamula, Richard B. Fair, "An integrated digital microfluidic lab-on-a-chip for clinical diagnostics on human physiological fluids," Lab on a Chip, vol. 4, pp. 310-315, 2004.

Vijay Srinivasan, Vamsee K. Pamula, Richard B. Fair, "Droplet-based microfluidic lab-on-a-chip for glucose detection," Analytica Chimica Acta, vol. 507, No. 1, pp. 145-150, 2004.

V. Srinivasan, V.K. Pamula, P. Paik, and R.B. Fair, "Protein Stamping for MALDI Mass Spectrometry Using an Electrowetting-based Microfluidic Platform," Lab-on-a-Chip: Platforms, Devices, and Applications, Conf. 5591, SPIE Optics East, Philadelphia, Oct. 25-28, 2004.

Vijay Srinivasan, Vamsee K. Pamula, Michael G. Pollack, and Richard B. Fair, "Clinical diagnostics on human whole blood, plasma, serum, urine, saliva, sweat, and tears on a digital microfluidic platform," Proc. Micro Total Analysis Systems (mTAS), pp. 1287-1290, 2003.

Vijay Srinivasan, Vamsee K. Pamula, Michael G. Pollack, and Richard B. Fair, "A digital microfluidic biosensor for multianalyte detection", Proc. IEEE 16th Micro Electro Mechanical Systems Conference, pp. 327-330, 2003.

Vijay Srinivasan, Vamsee K. Pamula, K. Divakar Rao, Michael G. Pollack, Joseph A. Izatt, and Richard B. Fair, "3-D imaging of moving droplets for microfluidics using optical coherence tomography," Proc. Micro Total Analysis Systems (mTAS), pp. 1303-1306, 2003.

F. Su, S. Ozev and K. Chakrabarty, "Testing of droplet-based microelectrofluidic systems", Proc. IEEE International Test Conference, pp. 1192-1200, 2003.

Nicole Weaver, "Application of Magnetic Microspheres for Pyrosequencing on a Digital Microfluidic Platform", dated 2005.

PCT International Preliminary Report on Patentability for PCT/US2005/030247 dated Feb. 28, 2007.

PCT International Search Report and Written Opinion for PCT/US2006/047486 dated May 2, 2008.

PCT International Search Report and Written Opinion for PCT/US2006/047481 dated May 5, 2008.

PCT International Search Report and Written Opinion for PCT/US2007/011298 dated Jun. 25, 2008.

PCT International Search Report and Written Opinion for PCT/US2007/009379 dated Aug. 18, 2008.

"Chip mixes droplets faster", MIT Technology Review, Oct. 2003.

"Chip Juggles Droplets", Technology Research News, Sep. 4-11, 2002.

"Laboratory on a Chip", Popular Mechanics, Mar. 2002.

"Lab-on-a-Chip Technology May Present New ESD Challenges", Electrostatic Discharge Journal, Mar. 2002.

"Making materials fit the future: accommodating relentless technological requirements means researchers must recreated and reconfigure materials, frequently challenging established laws of physics, while keeping an eye on Moore's law", R&D Magazine, Dec. 2001.

Vijay Srinivasan, Anand Jog and Richard B. Fair, "Scalable Macromodels for Microelectromechanical Systems", Technical Proc. 2001 Int. Conf. on Modeling and Simulation of Microsystems, pp. 72-75, 2004.

Ali Agah, "DNA Analysis Chip by Electrowetting Actuation," Stanford Nanofabrication Facility, p. 9, 2002.

Bhansali et al., "Resolving chemical/bio-compatibility issues in microfluidic MEMS systems," SPIE Conference on Microfluidic Devices and Systems II, vol. 3877, Santa Clara, CA, pp. 101-109 (1999).

Cho et al., "Concentration and binary separation of micro particles for droplet-based digital microfluidics," Lab Chip, vol. 7, pp. 490-498, 2007.

Lehmann et al., "Droplet-Based DNA Purification in a Magnetic Lab-on-a-Chip," Angewandte Chemie, vol. 45, pp. 3062-3067, 2006.

N. Pamme, "Magnetism and microfluidics," Lab on a Chip (LOC), vol. 6, pp. 24-38, 2006.

Juergen Pipper et al., "Clockwork PCR Including Sample Preparation," Angew. Chem. Int. Ed., vol. 47, pp. 3900-3904, 2008.

Olivier Raccurt et al., "On the influence of surfactants in electrowetting systems," J. Micromech. Microeng., vol. 17, pp. 2217-2223 (2007).

Jean-Maxime Roux and Yves Fouillet, "3D droplet displacement in microfluidic systems by electrostatic actuation," Sensors and Actuators A, vol. 134, Issue 2, pp. 486-493, Mar. 15, 2007.

R. Sista, "Development of a Digital Microfluidic Lab-on-a-Chip for Automated Immunoassay with Magnetically Responsive Beads", PhD Thesis, Department of Chemical Engineering, Florida State University, 2007.

E. Verpoorte, "Beads and chips: new recipes for analysis," Lab on a Chip (LOC), vol. 3, pp. 60N-68N, 2003.

Y. Wang et al., "Effcient in-droplet separation of magnetic particles for digital microfluidics," Journal of Micromechanics and Microengineering, vol. 17, pp. 2148-2156 (2007).

Masao Washizu, "Electrostatic Actuation of Liquid Droplets for Micro-Reactor Applications", IEEE Industry Applications Society Annual Meeting, pp. 1867-1873, Oct. 5-9, 1997.

Wheeler et al., "Electrowetting-on-dielectric for analysis of peptides and proteins by matrix assisted laser desorption/ionization mass spectrometry," Solid-State Sensor, Actuator and Microsystems Workshop publication, pp. 402-403, Jun. 6-10, 2004.

Aaron R. Wheeler, "Putting Electrowetting to Work," Science, vol. 322, No. 5901, pp. 539-540, Oct. 24, 2008.

Yi et al., "Geometric surface modification of nozzles for complete transfer of liquid drops," Solid-State Sensor, Actuator and Microsystems Workshop, pp. 164-167, Jun. 6-10, 2004.

* cited by examiner

DROPLET ACTUATOR ANALYZER WITH CARTRIDGE

1 RELATED APPLICATIONS

This application is a continuation of International Patent Application No. PCT/US2007/011298, entitled "Droplet Manipulation Systems," filed May 9, 2007, pending, which claims the benefit of, is related to, and incorporates by reference related provisional U.S. Patent Application Nos. 60/746,797, entitled "Portable Analyzer Using Droplet-Based Microfluidics," filed on May 9, 2006 and 60/806,412, entitled "Systems and Methods for Droplet Microactuator Operations," filed on Jun. 30, 2006.

2 GRANT INFORMATION

This invention was made with government support under DK066956, GM072155, HG003706, AI066590 awarded by National Institutes of Health; and under NNJ06JD53C awarded by NASA. The government has certain rights in the invention.

3 FIELD OF THE INVENTION

Embodiments of the present invention relate to a droplet actuator with cartridge, which may be provided as a portable or hand-held device. Embodiments may be conveniently used to provide analysis at the point of sample collection and may be useful, for example, for monitoring, testing, and/or analyzing in medical, environmental (e.g., for biological and/or chemical attack), agricultural, and industrial settings.

4 BACKGROUND OF THE INVENTION 4.1 Microfluidics Systems

Over the past several years researchers have made advances in microfluidics based upon manipulation of individual droplets through direct electrical control. Examples of such systems can be found in U.S. Pat. No. 6,911,132 and U.S. Patent Application Publication No. 2004/0058450, both to Pamula et al. These patent documents describe an apparatus for electrically manipulating droplets. Wixforth, U.S. Pat. No. 6,777,245, assigned to Advalytix AG (Munich) has described a technology that is reported to have the capability to electronically control chemical reactions on the surface of a biochip using surface acoustic waves generated by applying radio-frequency electric pulses to the chips. Gascoyne and others in U.S. Patent Publications 2005/0072677, 2004/0178068, 2004/0011651, 2003/0173223, 2003/0171325, 2003/0102854, and 2002/0036139, have reported the use of dielectrophoresis to manage the movement of a material or an object through a body of fluid. Patents and patent publications assigned to Fluidigm have described a technology based on fluid-control valves and interconnected channels that form networks of discrete pathways and intermediate switches. Labcyte Inc., U.S. Pat. No. 6,416,164 and other patents, describes the use of focused acoustic energy (ultrasound) to eject small droplets of liquid from open wells for its products that target sub-microliter transfer volumes. HandyLab has reported the development of a microfluidic system that relies on internally generated pressure—thermo-pneumatic pumps—to create and propel nanoliter-sized liquid plugs through a micro-channel network in which multiple discrete plugs function independently of each other. There remains a need in the art for systems that can be used to directly control these droplet microactuators, systems that can be used to develop and troubleshoot software for controlling droplet microactuators, and software languages for controlling droplet microactuators and components of droplet microactuator systems.

Microfluidic systems can be broadly categorized into continuous-flow and discrete-flow based architectures. Continuous-flow systems rely on liquid that is continually fed into the system (think of pipes, pumps, and valves), whereas discrete-flow systems utilize droplets of liquid.

Continuous flow systems are limited by the fact that liquid transport is physically confined to permanently etched channels. The transport mechanisms used are usually pressure-driven by external pumps or electrokinetically-driven by high-voltages. These approaches involve complex channeling and require large supporting systems in the form of external pumps, valves and power supplies. These restrictions make it difficult to achieve high degrees of functional integration and control in conventional continuous-flow systems, particularly in realizing a handheld device at the point of sample collection. Moreover, the fluid flow is unidirectional and therefore is not easily reconfigurable or programmable.

In addition, the technological limitations of continuous-flow channel systems do not allow the integration of multiple formats of analysis such as PCR, immunoassays, chemistry, and cell handling together onto a single chip. Even where these technologies miniaturize the assay on a lab-on-a-chip they require a large instrument to manage even limited operations on the chip. Therefore, a need exists for a microfluidic lab-on-a-chip that can meet the needs of multifunctionality and portability demanded by POSC applications.

4.2 Portable Analyzer Background

Point of sample collection testing is useful in a wide variety of contexts, from medical monitoring and diagnostics to environmental testing. In contexts, like medical monitoring or environmental monitoring of effluent streams, point of sample testing can minimize the time from sample collection to action taken. Moreover, in many instances it may be virtually impossible to preserve samples for transport to a central lab. Even when such preservation is possible, the extensive procedures required may render preservation and transport to a central lab economically unfeasible. Alternatively, researchers may be forced to accept some diminishment in accuracy of analysis caused by transport under less than ideal conditions.

Several groups have made or attempted to make systems that permit point of sample collection testing. For example, Lauks, U.S. Pat. No. 5,096,669, describes a sensing device for real time fluid analysis. Zelin, U.S. Pat. No. 5,821,399, describes a method for automatic fluid flow compensation in a disposable fluid analysis sensing device. In U.S. Pat. No. 5,124,661, Zelin et al. describe a reusable test unit for testing the functionality of a portable blood analyzer. Enzer et al., U.S. Pat. No. 4,436,610, describes an apparatus for measuring the hydrogen ion activity or pH value of blood. Cheng et al., U.S. Pat. Nos. 6,071,394, 6,403,367 and 6,280,590, and Sheldon et al., U.S. Pat. No. 6,129,828, all assigned to Nanogen Inc. (San Diego, Calif.), describe a device to perform separation of bacterial and cancer cells from peripheral human blood in microfabricated electronic chips by dielectrophoresis. Miles et al., U.S. Pat. No. 6,576,459, describes a sample preparation and analysis device which incorporates both immunoassays and PCR assays into a compact microchip. Biosite Inc. (San Diego, Calif.) sells a point-of-care testing product for a set of three immunoassays for detection of elevated cardiac markers related to heart attack (myoglobin, CK-MB, and troponin I) (http://www.biosite.com/products/cardio.aspx). Buechler et al., U.S. Pat. No. 6,074,616, describes a fluorometer with drive electronics for positioning the sample with respect to the optical components. Brennen et al., U.S. Pat. No. 6,632,400, describes a microfluidic device consisting of microfluidic channels, compartments, and flow control elements. Boecker et al., U.S. Pat. No. 6,966,880, describes a portable medical analyzer with a sampling module with integrated sample extraction device, a sample port for receiving body fluid, an assay sensor module for analysis of the body fluid, an analytical detector module with detection of information from the assay, and a communications module for transferring the information to a remote location via a wired or wireless network.

5 BRIEF DESCRIPTION OF THE INVENTION

Embodiments of the present invention relate to a droplet actuator with cartridge.

According to one embodiment, a sample analyzer is provided and comprises: (a) an analyzer unit comprising electronic or optical receiving means; (b) a cartridge comprising self-contained droplet handling capabilities; and wherein the cartridge is coupled to the analyzer unit by a means which aligns electronic and/or optical outputs from the cartridge with electronic or optical receiving means on the analyzer unit.

According to another embodiment, a sample analyzer is provided and comprises: (a) a sample analyzer comprising a cartridge coupled thereto; and (b) a means of electrical interface and/or optical interface between the cartridge and the analyzer, whereby electrical signals and/or optical signals may be transmitted from the cartridge to the analyzer.

6 DEFINITIONS

As used herein, the following terms have the meanings indicated.

"Activate" with reference to one or more electrodes means effecting a change in the electrical state of the one or more electrodes which results in a droplet operation. For example, an electrode can be activated by applying a DC potential; by applying an AC potential, so that the activated electrode has an AC potential and an unactivated electrode has a ground or other reference potential; and/or by repeatedly applying an electrical potential to an electrode and then inverting it. It should be noted that an AC mode can be effected by using software to rapidly switch between polarities of the outputs.

"Analyte," means a target substance for detection which may be present in a sample. Illustrative examples include antigenic substances, haptens, antibodies, proteins, peptides, amino acids, nucleotides, nucleic acids, drugs, ions, salts, small molecules, and cells.

"Bead," with respect to beads on a droplet microactuator, means any bead or particle capable of interacting with a droplet on or in proximity with a droplet microactuator. The bead may, for example, be capable of being transported in a droplet on a droplet microactuator; configured with respect to a droplet microactuator in a manner which permits a droplet on the droplet microactuator to be brought into contact with the bead, on the droplet microactuator and/or off the droplet microactuator. Beads may be any of a wide variety of shapes, such as spherical, generally spherical, egg shaped, disc shaped, cubical, irregular and other three dimensional shapes. Beads may be manufactured using a wide variety of materials, including for example, resins, and polymers. The beads may be any suitable size, including for example, microbeads, microparticles, nanobeads and nanoparticles. BioPlex beads, such as BioPlex 2200 beads of Bio-Rad Laboratories, are an illustrative embodiment. In some cases, beads are magnetically responsive; in other cases beads are not significantly magnetically responsive. For magnetically responsive beads, the magnetically responsive material may constitute substantially all of a bead or only one component of a bead. The remainder of the bead may include, among other things, polymeric material, coatings, and moieties which permit attachment of an assay reagent. Examples of suitable magnetically responsive beads are described in U.S. Patent Publication No. 2005-0260686, "Multiplex flow assays preferably with magnetic particles as solid phase," published on Nov. 24, 2005, the entire disclosure of which is incorporated herein by reference for its teaching concerning magnetically responsive materials and beads.

"Communicate" (e.g., a first component "communicates with" or "is in communication with" a second component) is used herein to indicate a structural, functional, mechanical, optical, electrical, or fluidic relationship, or any combination thereof, between two or more components or elements. As such, the fact that one component is said to communicate with a second component is not intended to exclude the possibility that additional components may be present between and/or operatively associated or engaged with, the first and second components.

"Chip" refers to any substrate including not only silicon or semiconductors but glass, printed circuit boards, plastics or any other substrate on which the droplets are manipulated.

"Droplet" means a volume of liquid on a droplet microactuator which is at least partially bounded by filler fluid. For example, a droplet may be completely surrounded by filler fluid or may be bounded by filler fluid and one or more surfaces of the droplet microactuator. Droplets may take a wide variety of shapes; nonlimiting examples include generally disc shaped, slug shaped, truncated sphere, ellipsoid, spherical, partially compressed sphere, hemispherical, ovoid, cylindrical, and various shapes formed during droplet operations, such as merging or splitting or formed as a result of contact of such shapes with one or more surfaces of a droplet microactuator.

"Droplet operation" means any manipulation of a droplet on a droplet microactuator. A droplet operation may, for example, include: loading a droplet into the droplet microactuator; dispensing one or more droplets from a source droplet; splitting, separating or dividing a droplet into two or more droplets; transporting a droplet from one location to another in any direction; merging or combining two or more droplets into a single droplet; diluting a droplet; mixing a droplet; agitating a droplet; deforming a droplet; retaining a droplet in position; incubating a droplet; heating a droplet; vaporizing a droplet; cooling a droplet; disposing of a droplet; transporting a droplet out of a droplet microactuator; other droplet operations described herein; and/or any combination of the foregoing. The terms "merge," "merging," "combine," "combining" and the like are used to describe the creation of one droplet from two or more droplets. It should be understood that when such a term is used in reference to two or more droplets, any combination of droplet operations sufficient to result in the combination of the two or more droplets into one droplet may be used. For example, "merging droplet A with droplet B," can be achieved by transporting droplet A into contact with a stationary droplet B, transporting droplet B into contact with a stationary droplet A, or transporting droplets A and B into contact with each other. The terms "splitting," "separating" and "dividing" are not intended to imply any particular outcome with respect to size of the resulting droplets (i.e., the size of the resulting droplets can be the same or different) or number of resulting droplets (the number of resulting droplets may be 2, 3, 4, 5 or more). The term "mixing" refers to droplet operations which result in more homogenous distribution of one or more components within a droplet. Examples of "loading" droplet operations include microdialysis loading, pressure assisted loading, robotic loading, passive loading, and pipette loading.

"Electronically coupled" or "coupled" in reference to electrical components is used herein to indicate an electrical or data relationship between two or more components or elements. As such, the fact that a first component is said to be electronically coupled to a second component is not intended to exclude the possibility that additional components may be present between, and/or operatively associated or engaged with, the first and second components. Further, electrically coupled components may in some embodiments include wireless intervening components.

"Highlight" used with reference to a user interface or the like, such as a droplet microactuator map as described herein, means that a component of the user interface or map may be visually differentiated, e.g., by a change in color, brightness, shading, shape, or by appearance/disappearance of a symbol, icon, or other visual identifier. For example, mousing over or selecting a representation of an electrode on the user interface may cause the electrode representation to change color. Sounds may also accompany highlighted items to further facilitate user interaction with the system.

"Input device" is used broadly to include all possible types of devices and ways to input information into a computer system or onto a network. Examples include stylus-based devices, pen-based devices, keyboard devices, keypad devices, touchpad devices, touch screen devices, joystick devices, trackball devices, mouse devices, bar-code reader devices, magnetic strip reader devices, infrared devices, and speech recognition technologies.

"Mouse over" means to associate a cursor or other selection device with an object on a user interface. Mousing over may be accomplished using a wide variety of input devices, such as a mouse, keyboard, or joystick, or a combination of such devices.

"Output device" is used broadly to include all possible types of devices and ways to output information or data from a computer system to a user or to another system. Examples include visual displays, LEDs, printers, speakers, modems and wireless transceivers.

"Protocol" means a series of steps that includes, but is not limited to, droplet operations on one or more droplet microactuators.

"Select" with reference to a user interactive element, such as icon, field, or virtual button, displayed on a user interface means to provide input which results in the execution of instructions associated with the object. Thus, for example, selection of a representation of an electrode displayed on a droplet microactuator map by pointing and clicking on the electrode representation may result in execution of instructions necessary for activating the actual electrode and/or instructions necessary for adding a line of code to a set of instructions which instructs activation of the actual electrode. Selection may be achieved using any of a variety of input devices or combination of input devices, such as mouse, joystick, and/or keyboard.

"Surface" with reference to immobilization of a molecule, such as an antibody or in analyte, on the surface, means any surface on which the molecule can be immobilized while retaining the capability to interact with droplets on a droplet microactuator. For example, the surface be a surface on the droplet microactuator, such as a surface on the top plate or bottom plate of the droplet microactuator; a surface extending from the top plate or from the bottom plate of the droplet microactuator; a surface on a physical object positioned on the droplet microactuator in a manner which permits it to interact with droplets on the droplet microactuator; and/or a bead positioned on the droplet microactuator, e.g., in a droplet and/or in a droplet microactuator but exterior to the droplet.

The terms "top" and "bottom" are used throughout the description with reference to the top and bottom substrates of the droplet microactuator for convenience only, since the droplet microactuator is functional regardless of its position in space.

When a given component such as a layer, region or substrate is referred to herein as being disposed or formed "on" another component, that given component can be directly on the other component or, alternatively, intervening components (for example, one or more coatings, layers, interlayers, electrodes or contacts) can also be present. It will be further understood that the terms "disposed on" and "formed on" are used interchangeably to describe how a given component is positioned or situated in relation to another component. Hence, the terms "disposed on" and "formed on" are not intended to introduce any limitations relating to particular methods of material transport, deposition, or fabrication.

When a liquid in any form (e.g., a droplet or a continuous body, whether moving or stationary) is described as being "on", "at", or "over" an electrode, array, matrix or surface, such liquid could be either in direct contact with the electrode/array/matrix/surface, or could be in contact with one or more layers or films that are interposed between the liquid and the electrode/array/matrix/surface.

When a droplet is described as being "on" or "loaded on" a droplet microactuator, it should be understood that the droplet is arranged on the droplet microactuator in a manner which facilitates using the droplet microactuator to conduct one or more droplet operations using on the droplet, the droplet is arranged on the droplet microactuator in a manner which facilitates sensing of a property of or a signal from the droplet, and/or the droplet has been subjected to a droplet operation on the droplet microactuator.

7 BRIEF DESCRIPTION OF THE DRAWINGS

8 DETAILED DESCRIPTION OF THE INVENTION

Figure 1:
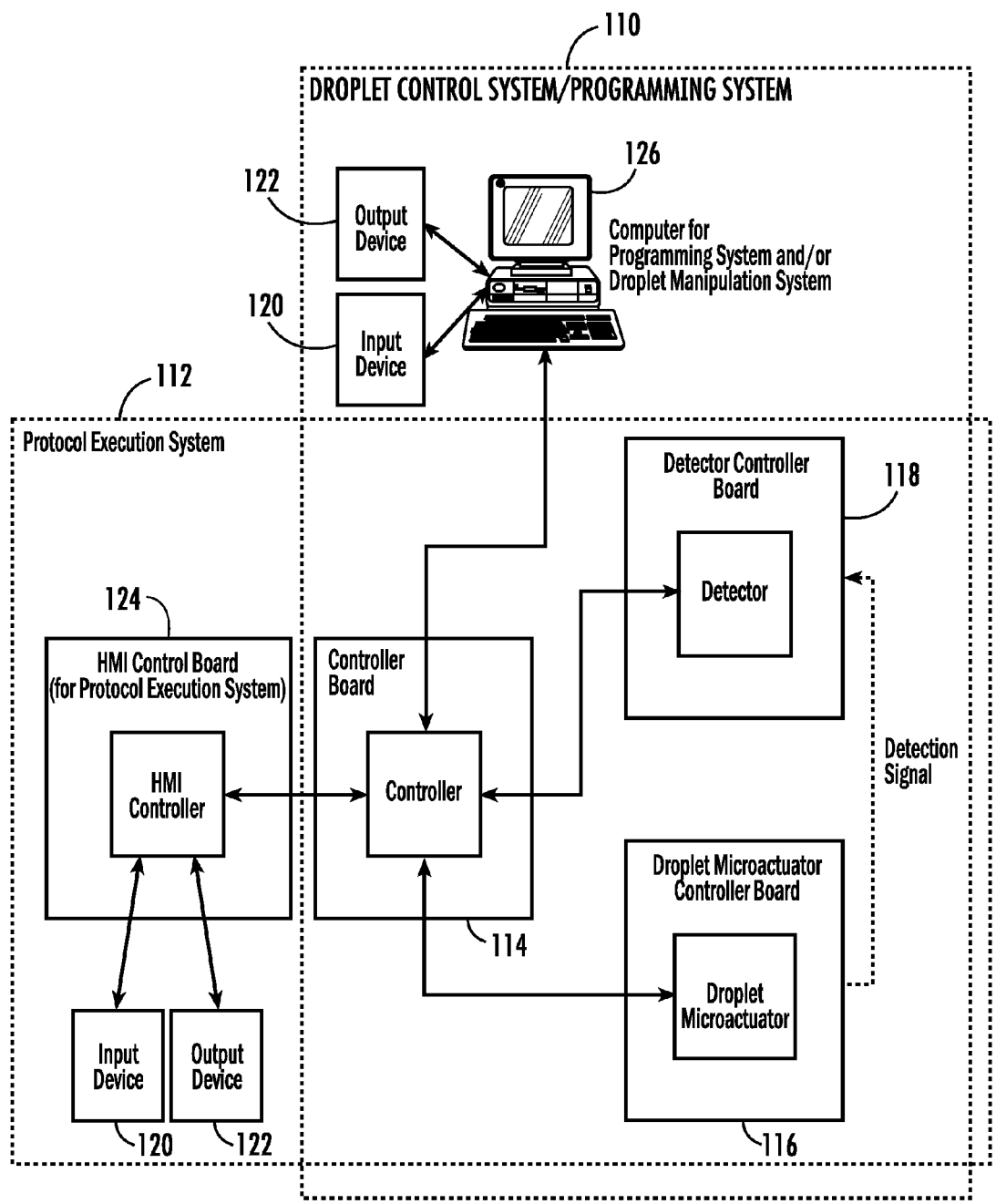
FIG. 1 is an illustration of droplet microactuator systems in accordance with an embodiment of the present invention.

The present invention relates to systems and methods for controlling droplet movements on a droplet microactuator, including software and systems for creating code for controlling droplet movements. The present invention also relates to a droplet microactuator device, system and method for processing and/or analyzing samples, including the provision of a portable or handheld device.

8.1 Systems and Methods for Droplet Microactuator Operations

One aspect of the present invention provides a droplet control system, a programming system, a protocol execution system, as well as integrated systems including the droplet control system, the programming system, and/or the protocol execution system. A method or computer useable instructions for controlling these systems is also provided. The droplet control system permits a user to control droplet microactuator system functions, such as droplet operations and detector operations. The programming system permits a user to develop software routines or computer useable instructions for controlling droplet microactuator system functions, such as droplet operations and detector operations. The protocol execution system permits a user to execute software routines that control droplet microactuator system functions, such as droplet operations and detector operations.

At a high level, each of the systems of the invention typically includes a processor or controller, a droplet microactuator, a detector (optional), input and output device(s), and software. The droplet control system includes droplet control software programmed to display a droplet control interface for controlling droplet microactuator system functions. The programming system includes programming software programmed to facilitate creation of a set of computer executable or computer useable instructions for controlling droplet microactuator system functions. The protocol execution system includes protocol execution software programmed to facilitate execution of a set of computer executable or computer useable instructions for controlling droplet microactuator system functions.

The systems may be provided as separate, independent systems. Two or more of the systems may be integrated into a single system. For example, the droplet control system and the programming system can be conveniently combined into a single system for controlling droplet microactuator system functions and creating software or code for controlling droplet microactuator system functions.

The ensuing sections discuss various aspects of the invention, starting in Section 8.1.1 with an overview of certain components of the systems, including the controller, the droplet microactuator, the detector, input and output devices, and software. Next, in Section 8.1.2, each of the three systems is discussed in further detail, including the droplet control system, the programming system, and the protocol execution system. Section 8.1.3 discusses the detector component of the systems in further detail. Section 8.1.4 discusses other methods associated with the systems of the invention. Finally, Section 8.3 discusses various aspects of the droplet microactuator and its operation as a component of the systems of the invention.

8.1.1 System Components

Droplet operations, detection, fluid loading, and other steps of an operations protocol may be accomplished using droplet microactuator systems, such as that illustrated in FIG. 1. Steps of various droplet operation protocols may be conducted using a droplet control system and/or programming system 110. A set of computer executable instructions may be written which can be loaded into a controller for execution of an operation protocol. Integrated systems including the droplet control system and/or programming system 110 and the protocol execution system 112 may also be used. The droplet control system and/or programming system 110 permit a user to control droplet microactuator system functions, such as droplet operations and sensor operations for fluid loading protocols. The protocol execution system 112 permits a user to execute software routines that control droplet microactuator system functions, such as droplet operations and fluid loading operations. The invention also provides a method or computer useable instructions for conducting these various processes or protocols. The programmable flexibility of the platform permits assays to be rapidly optimized and allows conditional execution steps to be implemented. For example, calibrations, confirmatory tests, or additional controls can be executed if triggered by a particular test result. In some embodiments, the system can integrate sample preparation steps. Automation of the system and on-droplet microactuator operations enhance portability and enable assays to be performed more quickly and by personnel with minimal training, thereby reducing human error.

Referring further to FIG. 1, at a high level, each of the systems of the invention typically includes a processor or controller 114, a droplet microactuator 116, a sensor or detector 118, input device(s) 120, output device(s) 122, and software. Input device(s) 120 and output devices 122 can be connected through a human-machine interface (HMI) controller 124. The droplet control system typically includes droplet control software run on a computer or processor 126 and programmed to display a droplet control interface for controlling droplet microactuator system functions. The protocol execution system 112 includes protocol execution software programmed to facilitate execution of a set of computer executable or computer useable instructions for controlling droplet microactuator system functions to conduct droplet operations, detection, fluid loading, and other protocols. The various components of this aspect are discussed in the ensuing sections.

8.1.1.1 Controller

The system of the invention may include a controller 114. The controller serves to provide processing capabilities, such as storing, interpreting, and or executing software instructions. The controller may, for example, be comprised of a digital signal processor (DSP) with memory, a microcontroller or an application specific integrated circuit (ASIC). An example of a suitable DSP processor is the Analog Devices Blackfin DSP processor.

The controller is electronically coupled to various hardware components of the invention, such as the droplet microactuator, any detectors, and any input and/or output devices. The controller may be configured and programmed to control data and/or power aspects of these devices. For example, with respect to the droplet microactuator, the controller controls droplet manipulation by activating/deactivating electrodes. This aspect of the invention is discussed further in Section 8.3.

As illustrated in FIG. 1, the controller 114 may further be electronically coupled to a separate computer system including a processor, input and output devices, data storage medium, and other components. This arrangement is particularly useful in the droplet control system and/or the programming system 110, in which the computer system is programmed to operate a droplet control user interface and/or a programming user interface. In this arrangement, the processor 126 of the computer system in one embodiment may accept input via the user interface and transmit instructions to the controller, e.g., to activate/deactivate electrodes, to read electrodes, memory, and/or detectors, and the like.

In the protocol execution system 112, software for controlling the system may be loaded directly into and executed by the controller to cause the controller to control the droplet microactuator system functions. In this embodiment, the system can run autonomously, e.g., as a portable or handheld system. Portable or handheld systems are discussed in more detail further hereinbelow.

Figure 2:
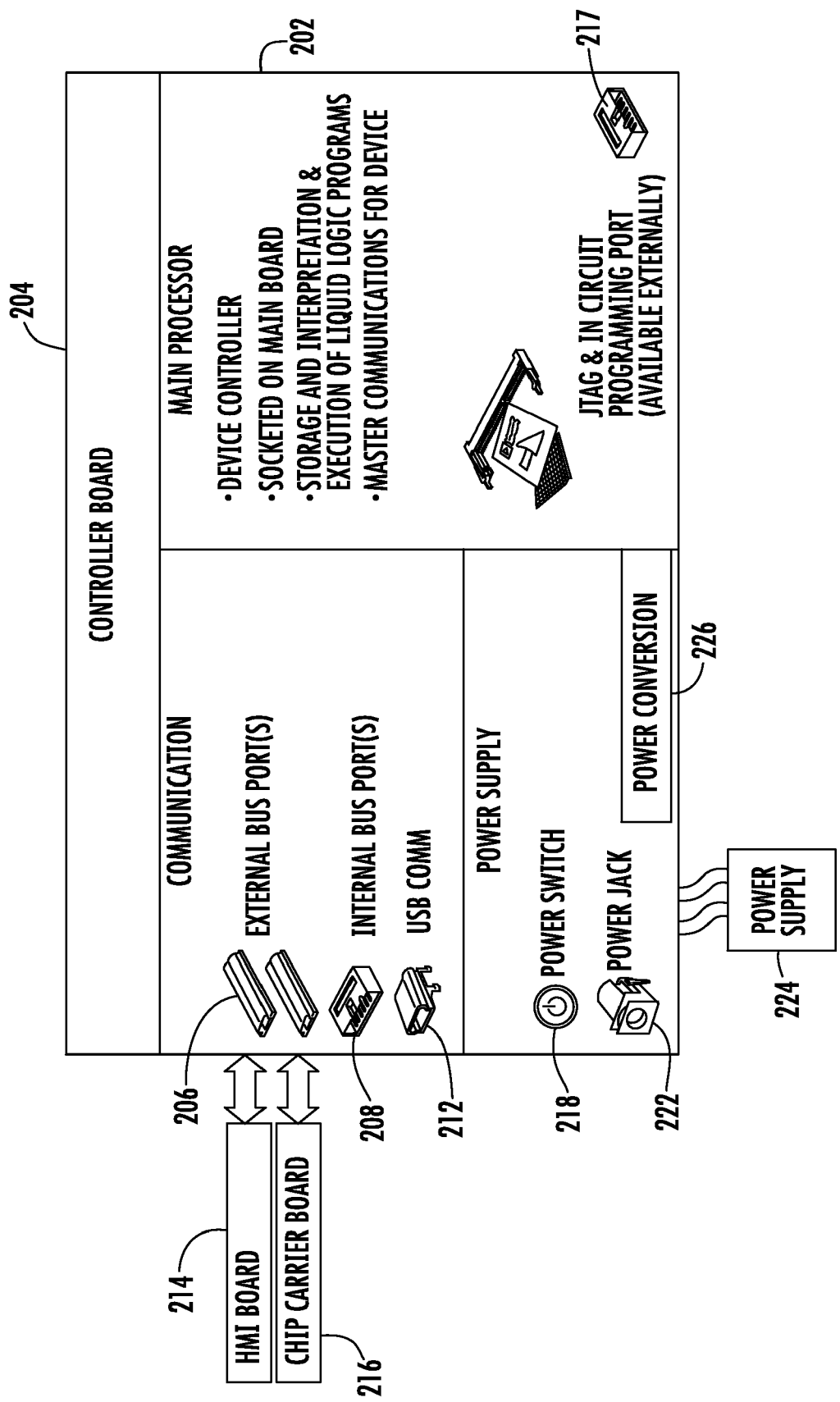
FIG. 2 is an illustration of a controller board in accordance with an embodiment of the present invention.

As illustrated in FIG. 2, the controller processor 202 may be provided as a component of a controller board 204. Controller processor 202 of controller board 204 is utilized for monitoring and controlling all other boards of the droplet microactuator system. The controller board 204 may include various internally and externally available communication ports electronically coupled to the processor, such as external bus port(s) 206, internal bus port(s) 208, and a USB comm port 212. External ports may connect the system to various input and output devices, such as a human-machine interface (HMI) controller board 214. An external port may be provided for coupling the controller board to a droplet microactuator controller board 216 for controlling and receiving output from the droplet microactuator. The controller board 204 may also include one or more test access ports and/or programming ports 217 (e.g., JTAG port) electronically coupled to the main processor.

The controller board 204 may also be coupled to a power switch 218, power jack 222, and power supply 224. Power conversion 226 functionality may also be included. The control board may be battery powered and/or coupled to an external source of power.

8.1.1.2 Droplet Microactuator

The system typically includes a droplet microactuator, as described further in Section 8.3. The droplet microactuator is electronically coupled to the processor such that the processor can control various operations of the droplet microactuator, such as droplet operations.

Figure 3:
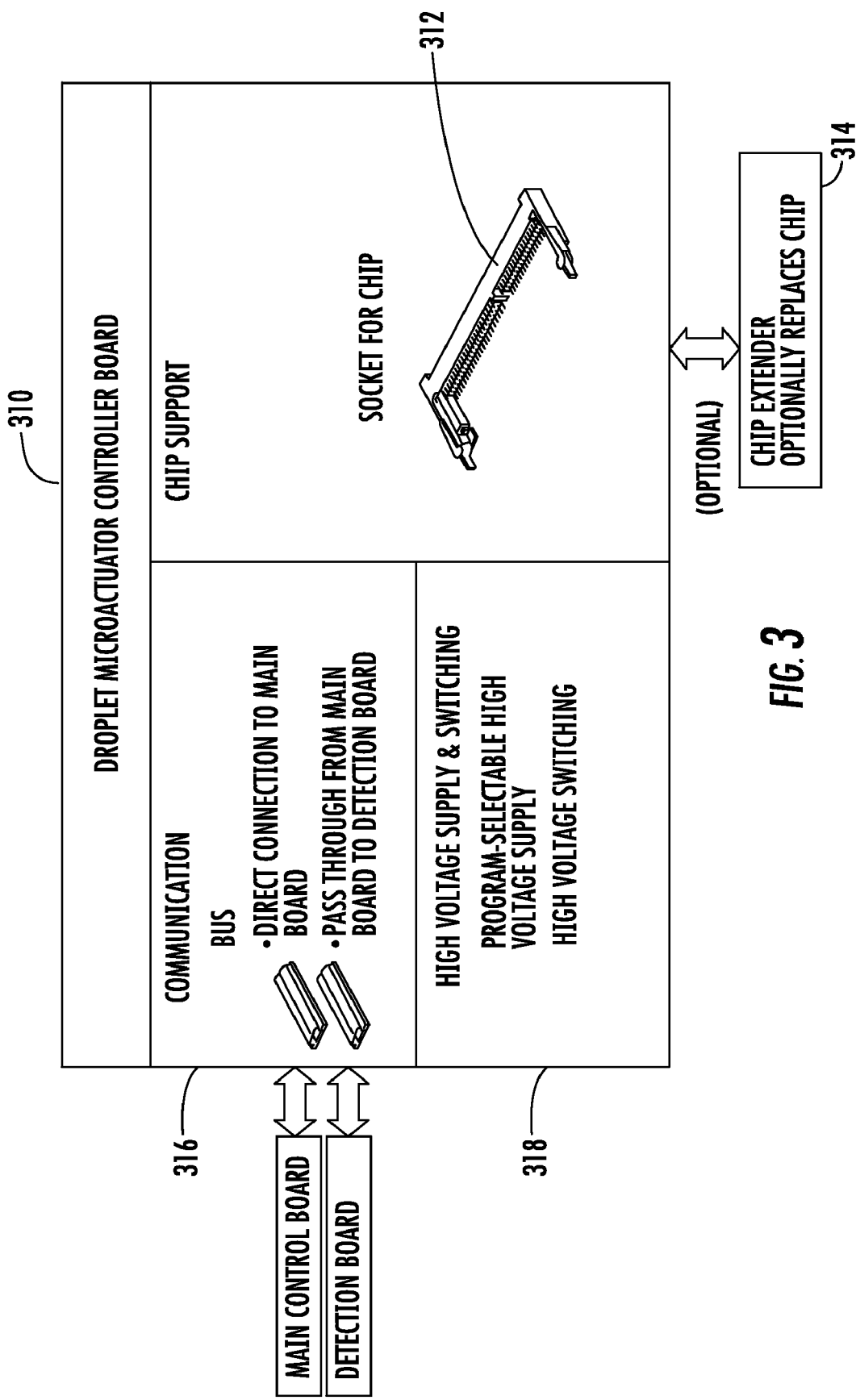
FIG. 3 is an illustration of a droplet microactuator controller board in accordance with an embodiment of the present invention.

FIG. 3 illustrates an embodiment of the invention in which the droplet microactuator is provided on a droplet microactuator controller board 310. The droplet microactuator controller board 310 generally includes a chip socket 312 or connector mechanism for electronically coupling the droplet microactuator that is installed on an external chip carrier board to droplet microactuator controller board 310. A chip extender 314 may also be provided. The droplet microactuator controller board 310 may also include communication components 316 for facilitating the electronic coupling of the droplet microactuator to the processor or may contain circuitry for conditioning or amplifying control signals arriving from the processor. The droplet microactuator controller board 310 may include power components 318 for supplying power to board components. Power components may, for example, include high voltage supply and switching components for supplying power to electrodes on the droplet microactuator. Aspects of the high voltage supply may include the ability to operate in one or more modes. For example, high voltage supply may operate in AC mode, which includes, for example, an AC Mode 1 (single-ended) and AC Mode 2 (duel-ended, bi-phase, or true AC). Additionally, feedback can be provided from the high voltage supply to, for example, controller processor 202 of controller board 204, in order to monitor, for example, for a fault detection (e.g., a power supply short on chip).

Figure 4:
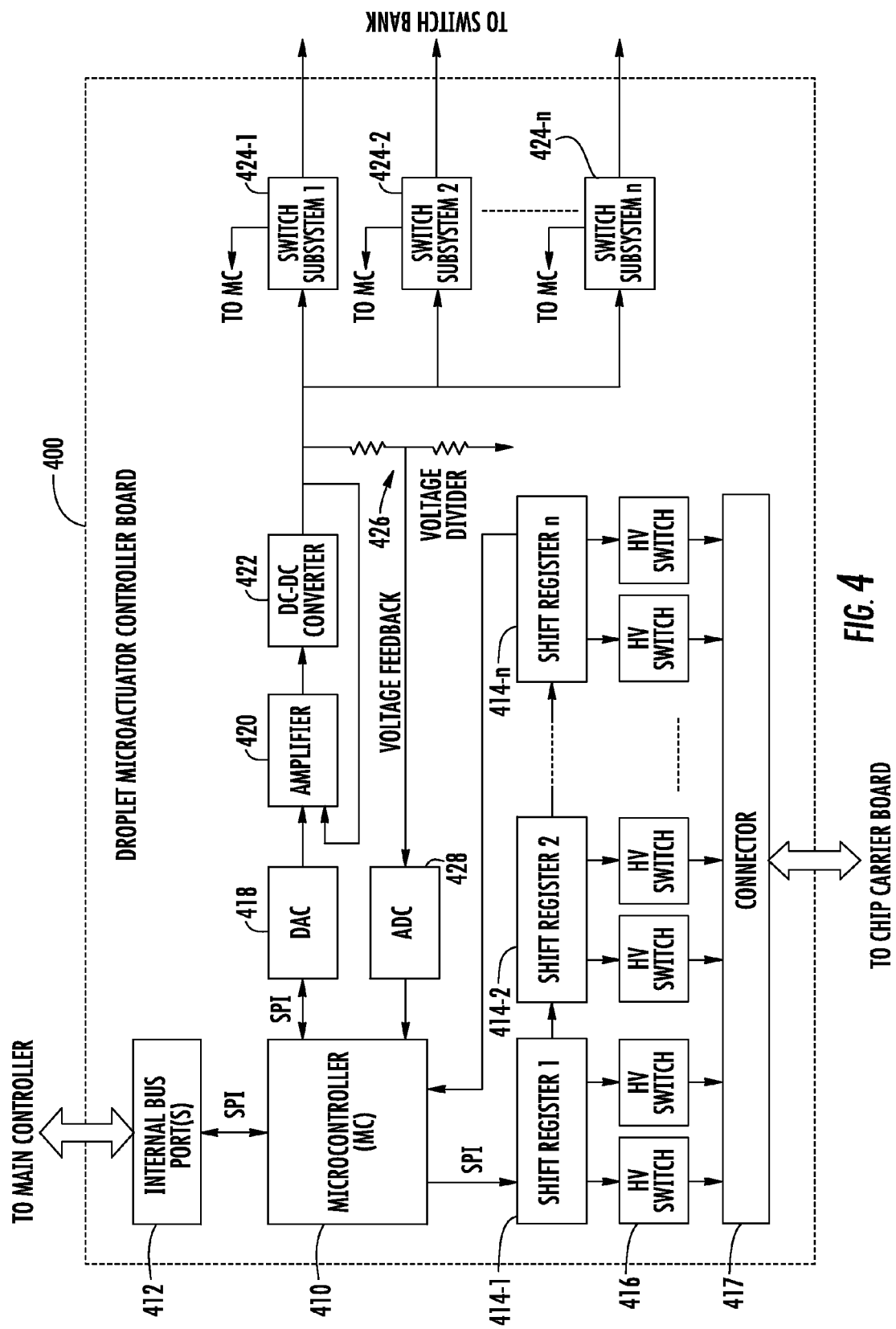
FIG. 4 is a block diagram of a microactuator controller in accordance with an embodiment of the present invention.

Another embodiment of a droplet microactuator controller board 400 is illustrated in FIG. 4. FIG. 4 illustrates a functional block diagram of microactuator controller board 400 that includes, for example, a microcontroller 410 that is able to communicate with controller processor 202 of controller board 204 via internal bus port(s) 412. Microcontroller 410 may be any processor or controller that is able to execute program instructions, such as program instructions for asserting electrodes and for setting voltages to certain levels. Microcontroller 410 may, for example, be comprised of a DSP with memory, a microcontroller or an ASIC. An example of a suitable DSP processor is the Analog Devices Blackfin DSP processor.

Microcontroller 410 is electronically coupled to one or more shift registers 414. In one example, microcontroller 410 is electronically coupled to shift registers 414-1, 414-2, through 414-n that are serially connected as shown in FIG. 4. An output of the final shift register 414, such as shift register 414-n, may be fed back to microcontroller 410. One or more outputs of each shift register 414 may be used to activate/deactivate one or more high voltage (HV) switches 416, the outputs of which are electronically coupled to a connector 417 for connecting to, for example, an external chip carrier board. Each HV switch 416 can be used for activating/deactivating one or more electrodes.

Additionally, microcontroller 410 is electronically coupled to at least one digital-to-analog converter (DAC) 418. DAC 418 performs a standard digital-to-analog conversion operation. In one example, DAC 418 is an x-bit DAC. Microcontroller 410 sets the electrowetting voltage by sending an SPI message to DAC 418 in the form of a digital voltage value. An analog output of DAC 418 feeds an analog input of an amplifier 420 that performs a standard voltage amplification operation of the analog voltage received from DAC 418. An analog output of amplifier 420 feeds an input of a DC-DC converter 422. DC-DC converter 422 is an adjustable power supply device, such as, but not limited to, the SMV12 300V device from Pico Electronics, Inc (Pelham, N.Y.), which is adjustable from about 0 volts to about 300 volts.

An analog output of DC-DC converter 422 feeds an input of one or more switch subsystems 424. In one example, DC-DC converter 422 feeds switch subsystems 424-1, 424-2, through 424-n, the outputs of which exit droplet microactuator controller board 400 for driving respective electrodes. Each switch subsystem 424 may switch to an AC mode, wherein an AC generator generates a square-wave signal of, for example, about 100 megahertz (MHz).

Additionally, each switch subsystem 424 may have a feedback line to microcontroller 410. Feedback to the microcontroller 410 can be placed at any stage in the power supply/switching train for, but not limited to, any of the following reasons. A first reason is to monitor supply voltage. This can be done before switching subsystems 424, or after, depending on whether or not the user wants to monitor losses incurred in the switches. A second reason is to monitor switch function. A voltage feedback at the output of a switch can indicate whether or not switching action is actually occurring, which is useful for diagnostic/fault detection/reroute purposes. A third reason is to serve as a sensor. The current incarnation of capacitance detection typically depends on such a feedback at the electrode that controls the droplet microactuator top plate as a sensor for capacitive coupled energy that gets coupled through the droplet.

Additionally, DC-DC converter 422 may have a current limit. In one example, DC-DC converter 422 has a maximum current ratting of about 4 milliamps (ma). A voltage feedback line from DC-DC converter 422 is provided to microcontroller 410 via a voltage divider circuit 426 and an analog-to-digital converter (ADC) 428. In the event of a fault condition wherein the current may rise above 4 ma, microcontroller 410 may limit or shutdown completely the output voltage of DC-DC converter 422, in order to prevent an over-current condition that may damage the electronics of droplet microactuator controller board 400. Additionally, in response to a fault condition, microcontroller 410 may set switch subsystems 424 to a high-impedance state, turn off HV switches 416, and set a FLAG signal to controller processor 202 of controller board 204. Further operation may be suspended until the fault condition is cleared.

Figure 5A:
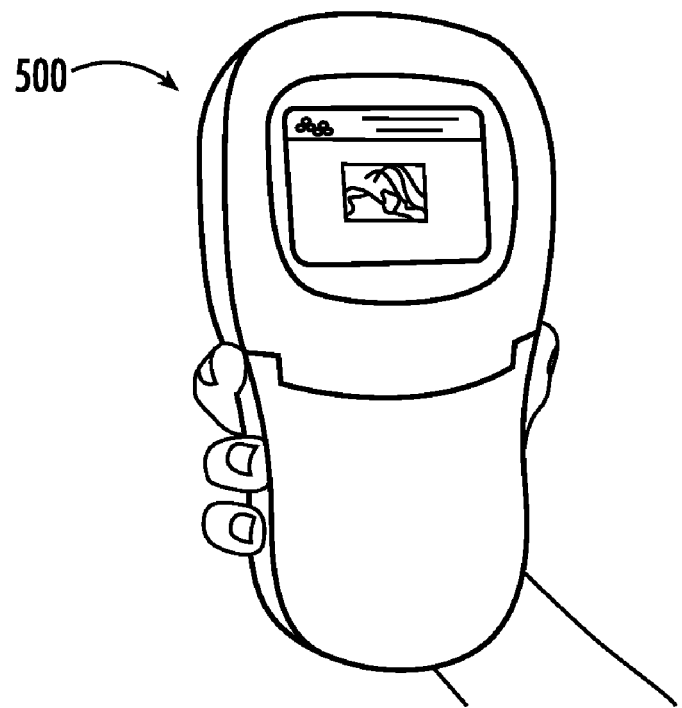
FIGS. 5A and 5B are illustrations of a portable handheld analyzer in accordance with an embodiment of the present invention.
Figure 5B:
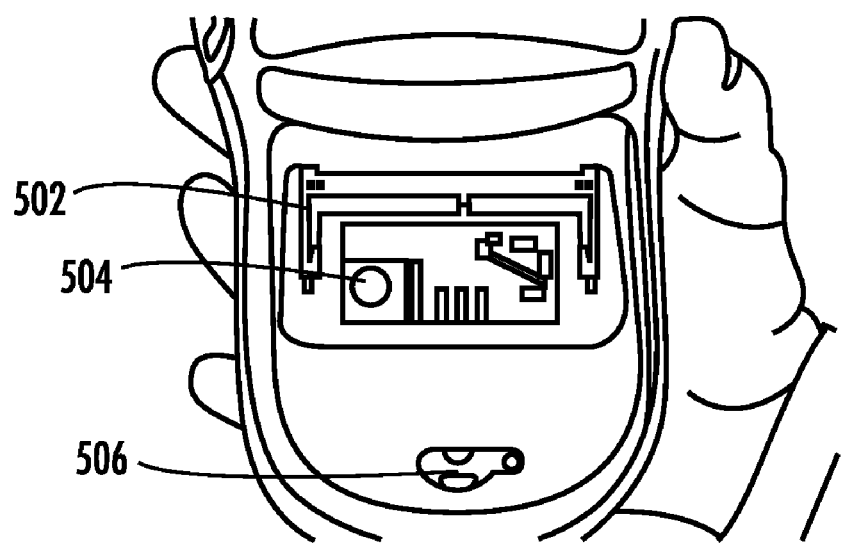

Referring to FIGS. 5A and 5B, in some embodiments, an analyzer can be provided as a portable device, such as a handheld device 500. FIG. 5A shows the exterior of handheld device 500 and FIG. 5B shows a chip carrier or slot 502 for insertion of a droplet microactuator (not shown), an optical sensor 504, such as a photomultiplier tube, for sensing optical signals from the droplet microactuator, and a lid latch 506, which may be coupled to the system to indicate whether the lid is open or closed. It is envisioned that the portable analyzer may also be a tabletop device. The portability of the droplet microactuator systems of the invention facilitates point of care or point of sample collection use in a wide variety of settings in clinics, operating rooms, emergency rooms, small laboratories, and in the field (emergency response teams, accidents, disasters, battlefield, bioterrorism sites etc.) for rapid diagnostics that can lead to quick turn around times in critical situations. Detailed aspects of portable systems contemplated herein are discussed hereinbelow, such as with reference to Section 8.2.

Figure 6:
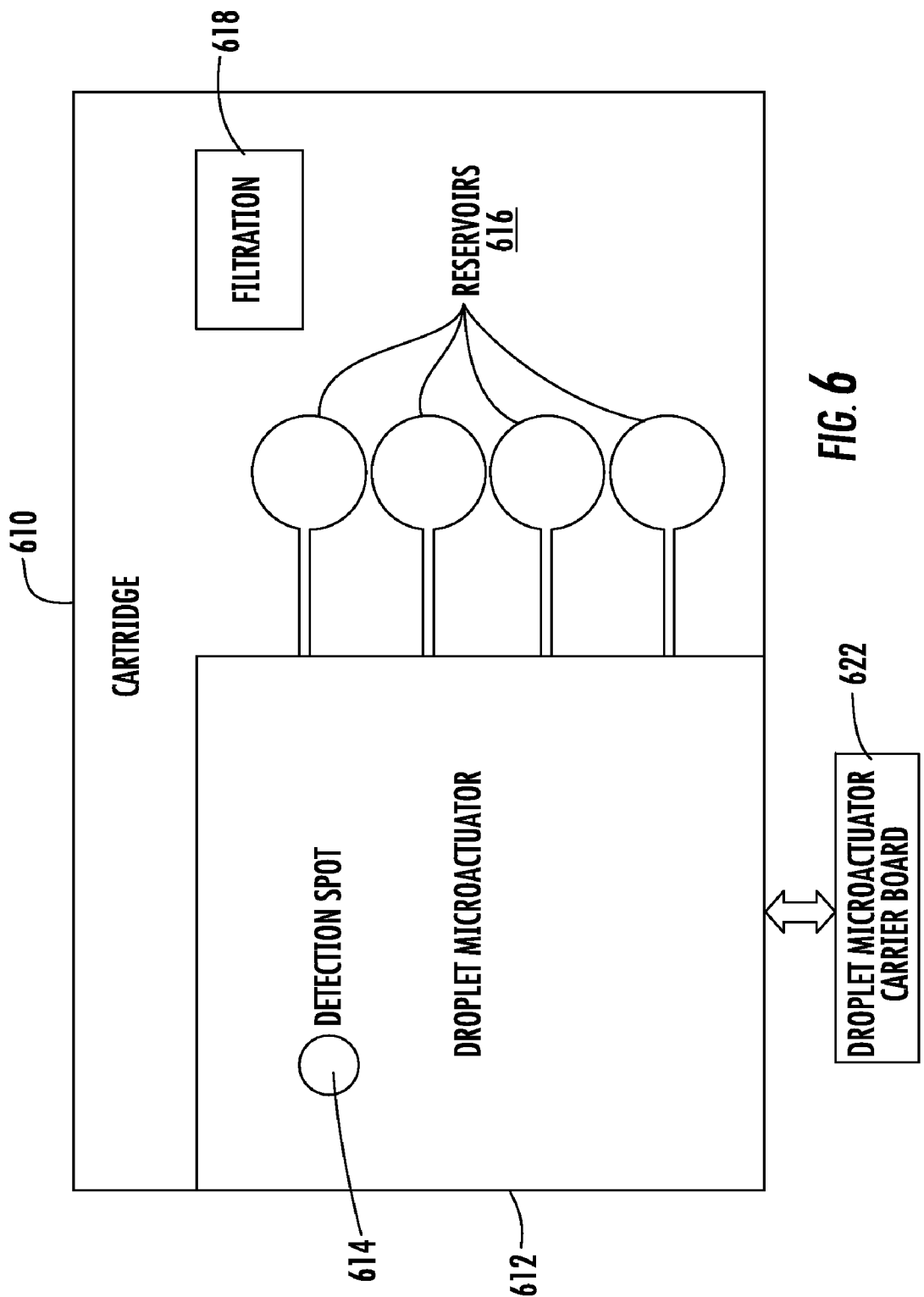
FIG. 6 is an illustration of a droplet microactuator and cartridge in accordance with an embodiment of the present invention.

Further, as illustrated in FIG. 6, the droplet microactuator may be provided as a component of a cartridge 610. The cartridge 610 may include the droplet microactuator 612 along with components such as a detection spot 614 for output of a signal to a detector; reservoirs 616 for assay inputs, such as reagents, magnetic beads, cleaning fluids, and/or controls; reservoirs for filler fluids; fluidic inputs and filtration components 618. In one example, the filtration component may be filter paper in combination with a reservoir. In use, for example, liquid, such as blood, can be blotted onto the filter paper and then seeps into the reservoir and then is drawn into the microactuator via electrowetting. The cartridge 610 may communicate with a droplet microactuator carrier board 622. The droplet microactuator can be mounted directly in the cartridge or, optionally, can be cabled to a chip carrier. Cartridges as contemplated herein are discussed further hereinbelow with reference to Section 8.3.3.

8.1.1.3 Detector

Figure 7:
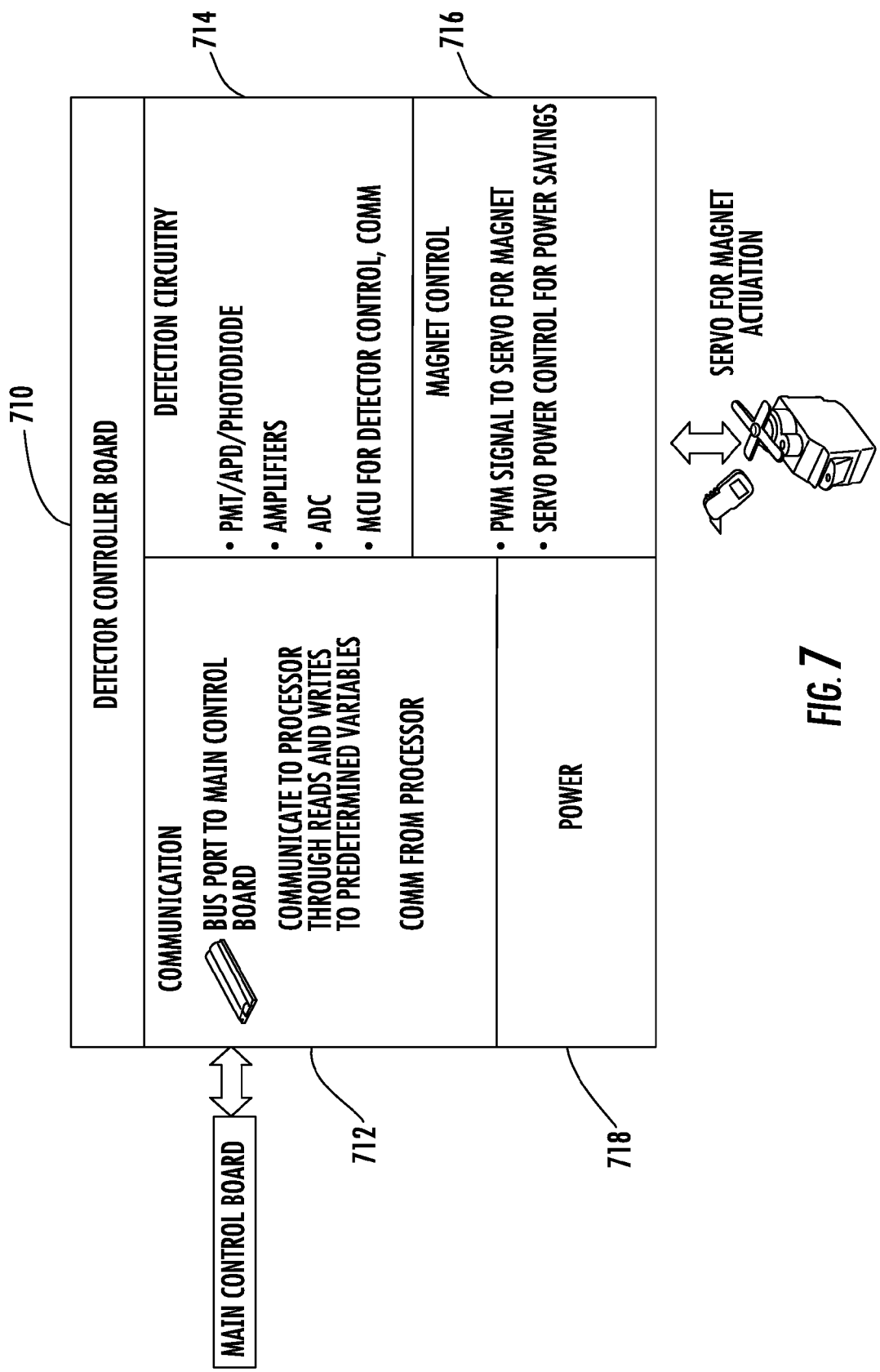
FIG. 7 is an illustration of a detector controller board in accordance with an embodiment of the present invention.

Various embodiments of the invention make use of detectors, as described further in Section 8.1.3. Detectors may include sensors which are coupled to or positioned in proximity to the droplet microactuator for the purpose of measuring parameters of interest on the droplet microactuator such as the fluorescent or luminescent intensity at a location on the chip where a reaction product may be located. Detectors may also include sensors which monitor the status of the system such as chip insertion sensors, lid latch sensors, ambient temperature sensors and the like. Ideally, output from each detector is mapped to a specific memory location, and the processor must only query the mapped location to obtain a reading from the detector. Detectors may be provided as components of a detector controller board 710, as illustrated in FIG. 7, which is described further in Section 8.1.3, "Detectors." Generally, detector controller board 710 can include communication ports 712 for communication with a main controller board. Detection circuitry 714 can also be included and can be any light sensor that returns results as, for example, a voltage, a frequency, a count, or a pulse duration. A microcontroller of detector controller board 710 processes the result, which is then sent to, for example, controller processor 202 of controller board 204. The detector can be mounted relative to the droplet microactuator and/or electronically coupled to the droplet microactuator such that the detector can detect signals, such as electrical or light signals, from the droplet microactuator. A magnet control 716 can optionally be included for actuation at lower power. The detector controller board 710 may also include power supply elements 718.

Figure 8:
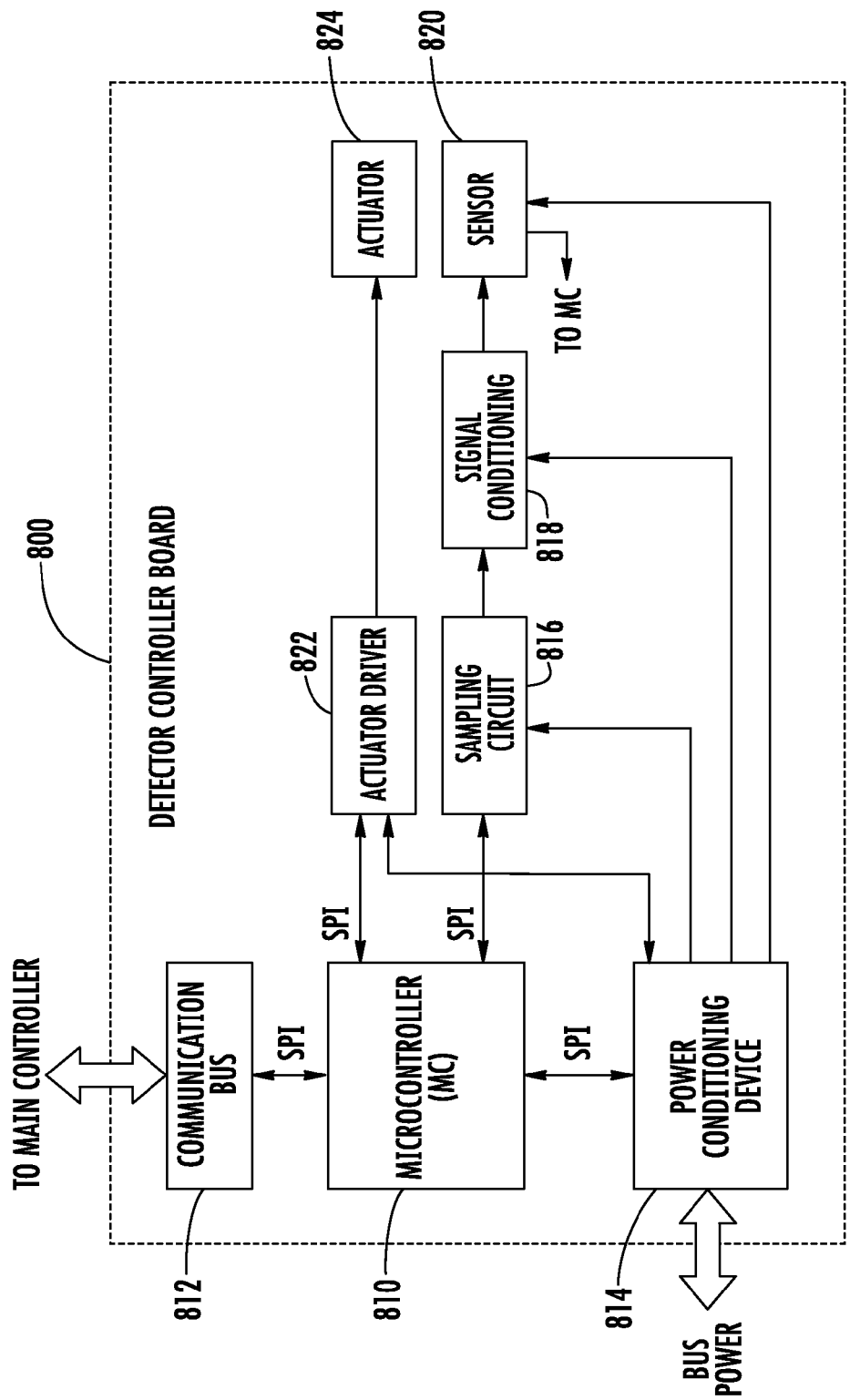
FIG. 8 is a block diagram of a detector controller board in accordance with an embodiment of the present invention.

FIG. 8 illustrates a functional block diagram of detector controller board 800 that includes, for example, a microcontroller 810 that is able to communicate, for example, with controller processor 202 of controller board 204 via internal bus port(s) 812. Microcontroller 810 may be any processor or controller that is able to execute program instructions, such as program instructions for processing the sensor data. Microcontroller 810 may, for example, be comprised of a DSP with memory, a microcontroller or an ASIC. An example of a suitable DSP processor is the Analog Devices Blackfin DSP processor.

Microcontroller 810 can be electronically coupled to a power conditioning device 814 and to a sampling circuit 816. Typically, an output of sampling circuit 816 is electrically connected to a signal conditioning device 818 that is electrically connected to a sensor 820. Additionally, microcontroller 810 is typically electronically coupled to an actuator driver 822 that is electrically connected to an actuator 824.

An output of power conditioning device 814 can be electrically connected to actuator driver 822. Alternatively, actuator driver 822 is not present and power conditioning device 814 can be directly connected to actuator 824. Another output of power conditioning device 814 is typically electrically connected to sampling circuit 816. Another output of power conditioning device 814 is typically electrically connected to signal conditioning device 818 and another output of power conditioning device 814 is electrically connected to sensor 820. Power conditioning device 814 is utilized to process the bus power in such a way as to be suitable for powering sampling circuit 816, signal conditioning device 818, sensor 820, and actuator driver 822.

Sampling circuit 816 may be, for example, but is not limited to, an analog-to-digital converter and/or a timer/counter. Signal conditioning device 818 may be, for example, but is not limited to, a signal conditioning device for use with a PMT (e.g., transimpedance amplifier), an APD (e.g., biased amplifier), a silicon photodiode (e.g., instrumentation amplifier), and any combinations thereof. Sensor 820 may be, for example, but is not limited to, an APD, a pin diode, a silicon photodiode, a PMT, an electrochemical cell, and any combinations thereof. In one example, the combination of actuator driver 822 and actuator 824 may represent, for example, but is not limited to, servos, solenoids, pumps, LEDs for florescence, and any combinations thereof.

Microcontroller 810 provides the overall control of detector controller board 800. For example, microcontroller 810 receives and processes commands of controller processor 202 of control board 204, such as returning data and providing control signals to the components of detector controller board 800. Microcontroller 810 has the intelligence to manage any actuator as it relates to any sensor and process the data returned from any sensor.

8.1.1.4 Input and Output Device(s)

Figure 9:
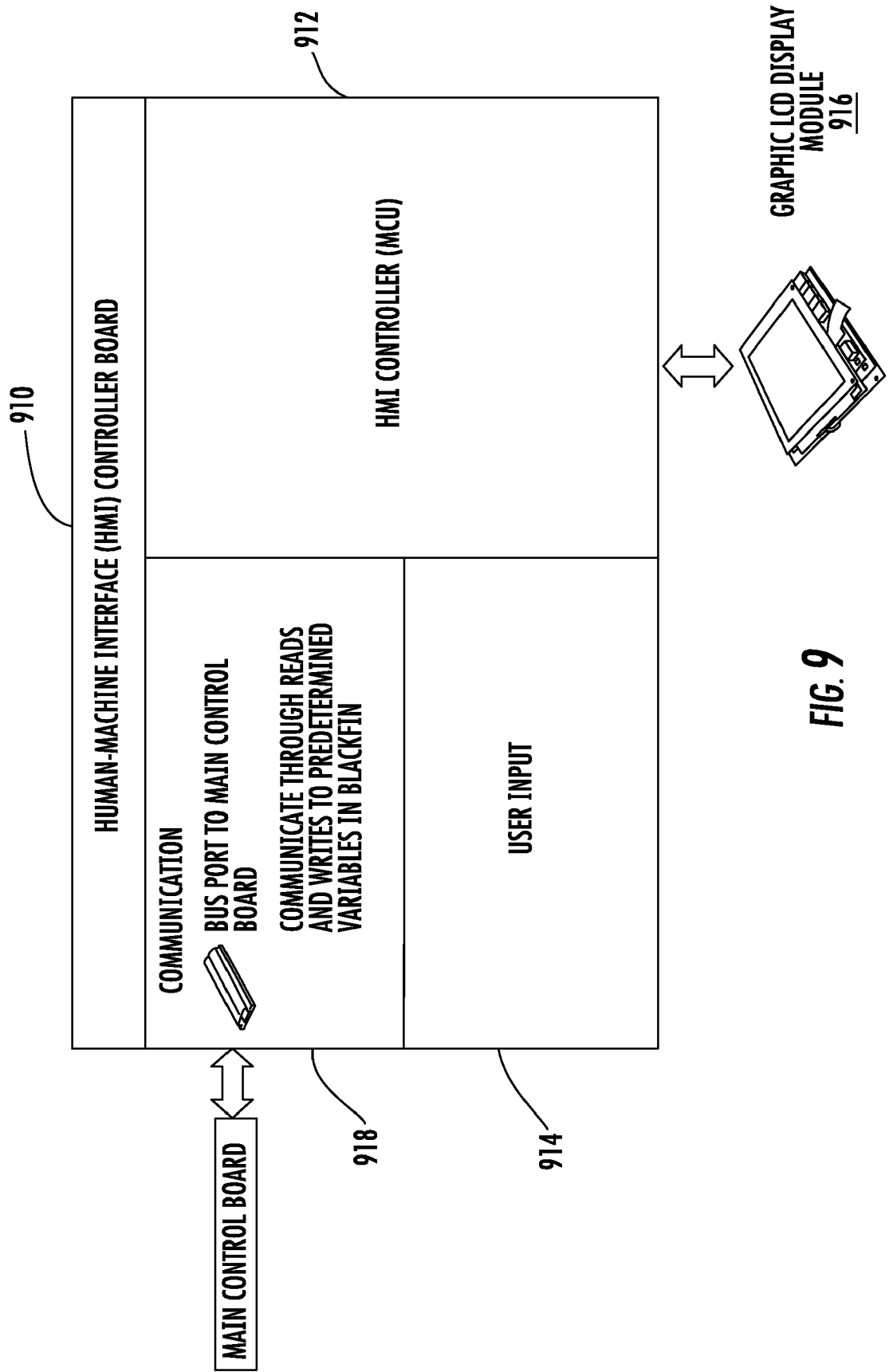
FIG. 9 is an illustration of a human-machine interface (HMI) controller board in accordance with an embodiment of the present invention.

Systems of the invention can also include various input devices and output devices. In certain embodiments, such as the protocol execution system, certain input and output devices may be controlled using a human-machine interface (HMI) controller board. For example, as illustrated in FIG. 9, an HMI controller board 910 may include an MCU controller 912 electronically coupled to input devices 914 and/or output devices 916, such as buttons, switches, keypads, LED indicators, touch screens, or an LCD display. The HMI controller board can be electronically coupled via communication ports 918 to the main processor, such as to controller processor 202 of control board 204.

8.1.1.5 Software

Each of the systems of the invention can include software, which is discussed further in Section 8.1.2. The software provided on a storage medium is one aspect of the invention. Examples of suitable storage mediums include magnetic storage, optical storage, phase-change memory, holographic storage, molecular memory storage, battery or capacitor-backed SRAM and flash memory storage. The software may be loaded in memory and/or in a processor. A system in which software of the invention is present in memory and/or a processor and/or a storage medium is also an aspect of the invention.

The software of the invention may be written in any of a variety of programming languages, such as Visual C, Java and/or Python. The system may include an interpreter for translating droplet manipulation and other instructions from the high-level language into an intermediate language for execution by the processor. Alternatively, software written according to the invention may be compiled into machine language using a compiler. The software interpreter and compiler for the language of the invention are themselves novel aspects of the invention. As such, all forms of data storage, memory, and processors containing the interpreter and/or compiler are aspects of the invention.

The system can be programmed to execute a wide variety of protocols involving any number of droplet manipulations. Multiple droplets can be independently and simultaneously manipulated on a single droplet microactuator. The capacity to independently manipulate multiple droplets in parallel enables execution of complex protocols as a series of basic microfluidic instructions. Systems are scalable and may control tens, hundreds, thousands or more parallel droplet manipulations per droplet microactuator chip. For example, at any one moment, up to a maximum of every control electrode on the droplet microactuator may be engaged in a droplet operation.

The system can be programmed to enable users to input instructions for the execution of protocols. Existing protocols may be monitored and adjusted according to user requirements. Complex protocols can be implemented in which the outcome of one or more steps determines the selection of one or more subsequent steps. For example, a droplet in which a certain measured result is positive may be transported for further processing, while a droplet in which a result is negative may be discarded, or vice versa.

8.1.2 Systems

The droplet control system includes droplet control software programmed to display a droplet control interface for controlling droplet operations on the droplet microactuator, controlling the detector, when present, and controlling other hardware associated with the droplet control system. The programming system includes software to facilitate creation of a set of software or computer useable instructions for controlling droplet microactuator system functions, such as droplet operations and/or detector operations.

Figure 10:
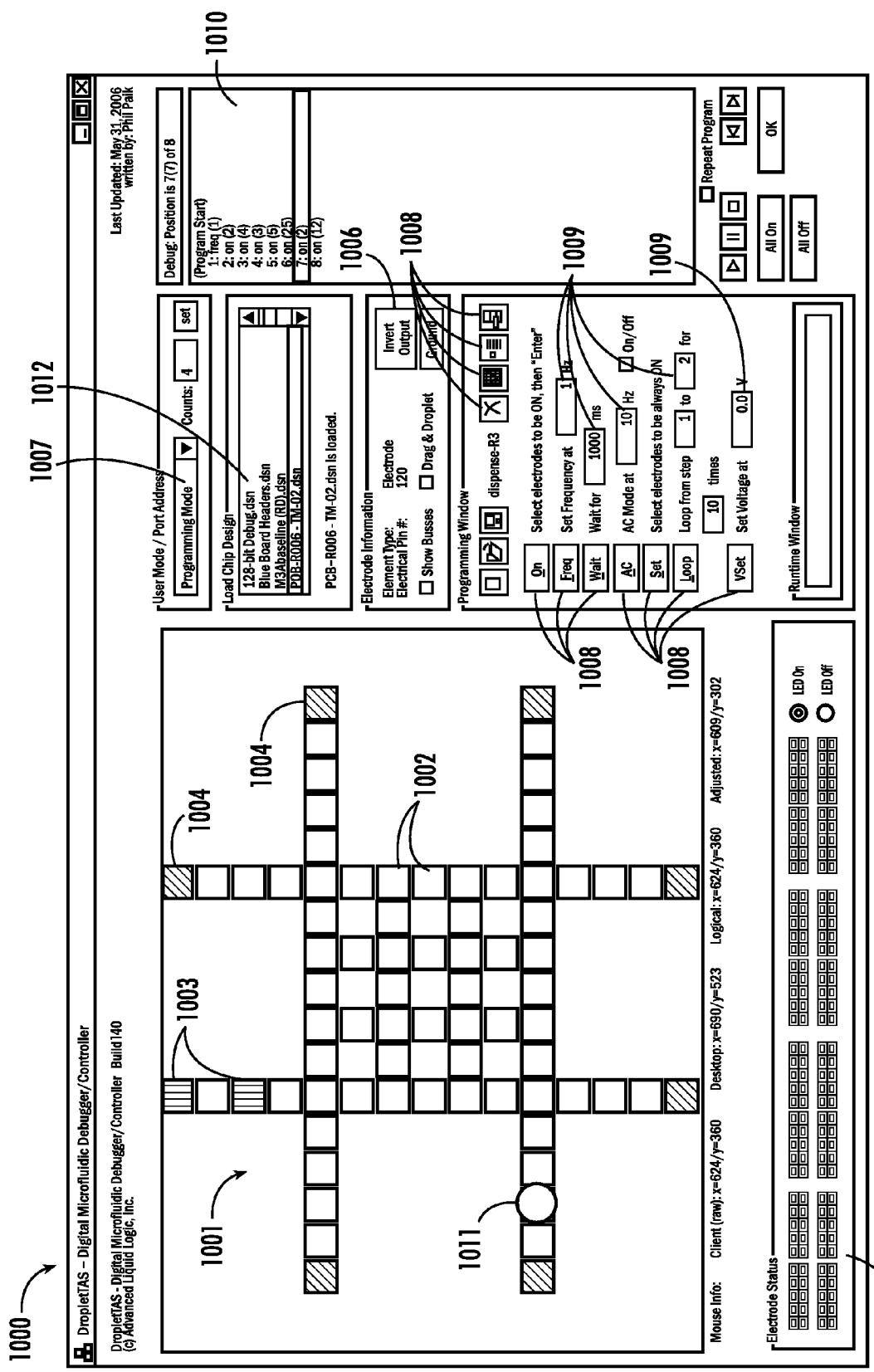
FIG. 10 is an illustration of a user interface of a droplet control system in accordance with an embodiment of the present invention.

The programming system may be integrated with or separate from the droplet control system. In an integrated system, droplet control functions and programming functions may be facilitated by a common user interface 1000, as illustrated in FIG. 10.

Both the droplet control system and the programming system include a user interface 1000. In both systems, the user interface may display a map 1001, preferably an interactive map, of a droplet microactuator. The map may be used to interact directly with the droplet microactuator to manipulate droplets on the droplet microactuator. The map may be used in a virtual mode to manipulate virtual droplets in a programming mode to develop and record subroutines for controlling droplet microactuator functions and related hardware. These and other aspects are discussed further in the ensuing sections.

8.1.2.1 Droplet Control System and User Interface

The droplet control system includes droplet control software. The droplet control software is programmed to display a droplet control interface for controlling droplet operations on the droplet microactuator, controlling the detector, when present, and controlling other hardware associated with the droplet microactuator system. The droplet control software permits a user to manipulate droplets on a droplet microactuator via a software driven user interface. An example of such an interface is illustrated in FIG. 10. Among other things, the user interface may permit a user to view information about a droplet microactuator. The user interface may also facilitate input by the user which controls functions of the droplet microactuator and associated devices, such as associated detectors.

With respect to controlling droplet operations on a droplet microactuator, the software is programmed, and the system is configured to, among other things, drive control and reference electrodes on the droplet microactuator to conduct the droplet operations. Droplet operations, which are discussed further in Section 8.3.8 below, are effected by applying a voltage, preferably high voltage, to selected electrodes. The software and system may be configured to permit software loaded in the processor to control firing of the selected electrodes by controlling the operation of relays associated with the electrodes.

As shown in FIG. 10, the user interface 1000, which can be displayed on an output device, may be programmed to display a graphical illustration or map 1001 of a droplet microactuator design. The map 1001 may be based on a matrix or other configuration that defines the position of each of the control electrodes and/or reservoirs. Components of the map may be differentiated by appearance, e.g., by shape, color, brightness, symbols, icons, etc. For example, in the map displayed in FIG. 10, unactivated droplet manipulation electrodes 1002 can be shown in a first color (such as gray), activated droplet manipulation electrodes and reservoirs 1003 can be shown in a second color (such as red), and unactivated reservoirs 1004 can be shown in a third color (such as blue).

In one embodiment, the matrix is defined in a control file which identifies a row and column for each electrode and/or reservoir. When a control file is loaded, the system reads in the matrix definitions and displays the corresponding map of the matrix on the user interface.

The interface may display information about components of the map, which may also be stored in the control file. In one embodiment, the system displays information about a component when it is moused over, selected, or otherwise electronically identified by a user. Information displayed may, for example, include some or all of the following information:
- component type, e.g., droplet manipulation electrode, reagent reservoir, sample reservoir, etc.;
- electrical connectivity information, e.g., electrode enumeration, grounds, pinout number etc.;
- adjacency relationships, e.g., in a polygonal electrode arrangement;
- representative geometry, for rendering the map in the user interface;
- design notes and/or other comments;
- part numbers;
- column and/or row position.

The system may also record the history of the activation of each electrode, so that the user may track the number of times an electrode has been activated. History information may, for example, be displayed by mousing over or selecting an electrode. The system may be programmed to accept input from a user instructing history information to be displayed simultaneously for all electrodes.

To facilitate user interaction, a moused over or selected electrode 1002 or other component may also cause the electrode or other component to be highlighted on the droplet microactuator map. This capability permits a user who is directly controlling droplet microactuator operations to review information about each potential step by mousing over the droplet microactuator component prior to actually selecting and activating the droplet microactuator component. The system may be programmed to highlight a moused over component and a selected component differently so that a user may differentiate between the two.

The programming system may include a selection means 1012 for permitting a user to select a droplet microactuator design or map for display. Alternatively, data identifying the droplet microactuator design or map may be included as a component of the droplet microactuator assembly or cartridge accessible by the system upon coupling of the droplet microactuator assembly or cartridge to the system.

It should be noted that in some designs, more than one electrode may be coupled to the same electrical output. Such designs can be used to simplify the electrical connections required for operating the droplet microactuator. In such designs, selecting or mousing over one electrode from a common set may result in selection, highlighting and activation of all electrodes in the set.

Thus, in one embodiment, the system is programmed so that when a user selects an unactivated electrode 1002 on a microactuator map 1001, the system activates the electrode. For example, the system may be programmed and configured so that clicking on a representation of an electrode on the map causes a voltage to be applied to a corresponding actual electrode on the droplet microactuator, thereby activating the selected electrode. In this way, a user can directly manipulate droplets on the droplet microactuator using the interface.

The droplet control system may permit a user to transport a droplet by sequentially clicking on a series of adjacent electrodes. Similarly, the system may permit a user to transport a droplet by selecting a virtual on-screen droplet and dragging the droplet to a virtual electrode at a desired location on the droplet microactuator map. Moreover, the system may permit a user to transport a droplet by selecting a virtual on-screen droplet, then clicking a virtual electrode at a desired location on the droplet microactuator map. In both examples involving virtual on-screen droplets, the system may be programmed to select a path and series of droplet operations for transporting the droplet from the starting location to the target location. For example, in some embodiments, the path selected may be the shortest possible path. It is understood that other droplet microactuator components may be similarly controlled via a user interface.

The system may be programmed to display a representation of the electrical control lines 1005 electronically coupled to the droplet microactuator components, so that when a user mouses over and/or selects a component, the system highlights the electrical control line that is supplying that component and/or other components supplied by the same control line.

The droplet microactuator may be visually monitored, e.g., using a microscope and video capture device. The user interface may be programmed to display a real-time image of the droplet microactuator from the video capture device. Further, the droplet microactuator map may be superimposed over the real-time droplet microactuator image so that a user can visualize droplet operations on the chip as he or she interacts with the chip via the user interface.

Similarly, the system may be programmed to display virtual droplets on the droplet microactuator map which illustrate actual behavior of droplets on a droplet microactuator which is being controlled by the system, and/or the system may be programmed to display virtual droplets on the droplet microactuator map which illustrate predicted behavior of droplets on a chip, even though a droplet microactuator is not being directly controlled by the system.

The system may also be programmed to effect an "inverse output" 1006 operation. In typical operation, the droplets are constantly connected to a ground voltage/ground line. In the "inverse output" operation, the signals are inverted so that the droplet is at a high voltage and the electrodes are activated by setting them to ground potential. In other words, the "inverse output" operation switches the polarity of the signals.

8.1.2.2 Programming System and User Interface

The programming system includes programming software programmed to facilitate creation of a set of software or computer useable instructions for controlling droplet operations on the droplet microactuator and controlling other functions of a droplet microactuator and related hardware. The software instructions, may for example, include instructions for executing a protocol for processing and analyzing a sample and outputting results of the analysis.

The programming system may be integrated with or separate from the droplet control system. FIG. 10 illustrates an integrated system in which droplet control functions and programming functions are facilitated by a common user interface.

The programming system may provide a programming mode to facilitate writing programs for controlling droplet microactuator functions and related components, such as detector components without interacting with an actual droplet microactuator chip. In the user interface exemplified in FIG. 10, the programming mode is selectable by a pull down menu 1007.

The programming system may, for example, include means for permitting a user to create a program with a set of instructions for execution by the droplet microactuator. Examples of suitable instructions include:
- "on" for identifying electrodes that are to be actuated;
- "frequency" to set the rate at which the steps are executed, e.g., the timing of electrode activation/deactivation;
- "wait" to permit the instructions to pause for a predetermined period;

"loop" to loop steps in the program;

"voltage" to set the voltage being applied to the outputs.

Instructions can be provided as a byte-coded language which includes instructions needed to conduct droplet manipulations and control other aspects of the system. The instructions prepared by the programming system can be recorded in the assembly language and assembled into byte codes. The byte codes can be loaded into a system of the invention, e.g., a protocol execution system, for execution. The system may include a software interpreter for interpreting the programming language for execution, e.g., in a protocol execution system.

In a preferred embodiment, the system can display a series of buttons or icons 1008 that can be selected to add, insert, update, modify or delete instructions from a subroutine. The buttons or icons may, as appropriate, be accompanied by fields 1009 for the entry of parameters associated with the instructions. For example, by clicking the "add" button, a command can be added at the end of a subroutine. By clicking an "insert" button, a command can be inserted within a subroutine. By clicking a "modify" button, a command present in a subroutine can be modified. By clicking a "delete" button, a command can be deleted. Further, a display field 1010, which may be editable, may be included for viewing, entering and/or editing code.

The programming system may also include a droplet microactuator map having one or more of the aspects described herein (e.g., see the description in Section 8.1.2.1, "Droplet Control System and User Interface").

The programming system may display a simulated execution of a subroutine on the droplet microactuator map, which outputs to the user a visual display of the effects of the command series selected. In other words, in a simulated execution mode, the software executes the steps of a subroutine but does not send an electrical signal to the droplet microactuator. In a preferred simulation mode, simulated droplets 1011 undergoing one or more droplet operations are displayed on the screen to illustrate to the user the actual effect of the program. In this way, a user can readily troubleshoot a subroutine without requiring interaction with a droplet microactuator.

The system may include a "repeat" mode in which a subroutine will continuously repeat itself until stopped by the user. Further, the system may include a "pause" command that enables a user to stop/start execution of a subroutine.

In one embodiment, droplet control functions and the programming functions are combined and controlled via a common set of one or more user interfaces. This embodiment may be configured so that a user can manually control steps on a droplet microactuator and the executed steps are translated into a subroutine that will execute the same steps on the droplet microactuator. In other words, the system may record manual droplet manipulations as a subroutine. The subroutine may later be uploaded and executed, e.g., on a protocol execution system. For example, the subroutine may be loaded in a portable or handheld protocol execution system so that the handheld system can execute a series of predetermined steps, e.g., steps required to process and analyze a sample.

In one embodiment, the invention provides an integrated tool with a click-and-drag droplet manipulation function and an assembler for generation of subroutines that can be stored and executed.

8.1.2.3 Protocol Execution System and User Interface

Figure 11:
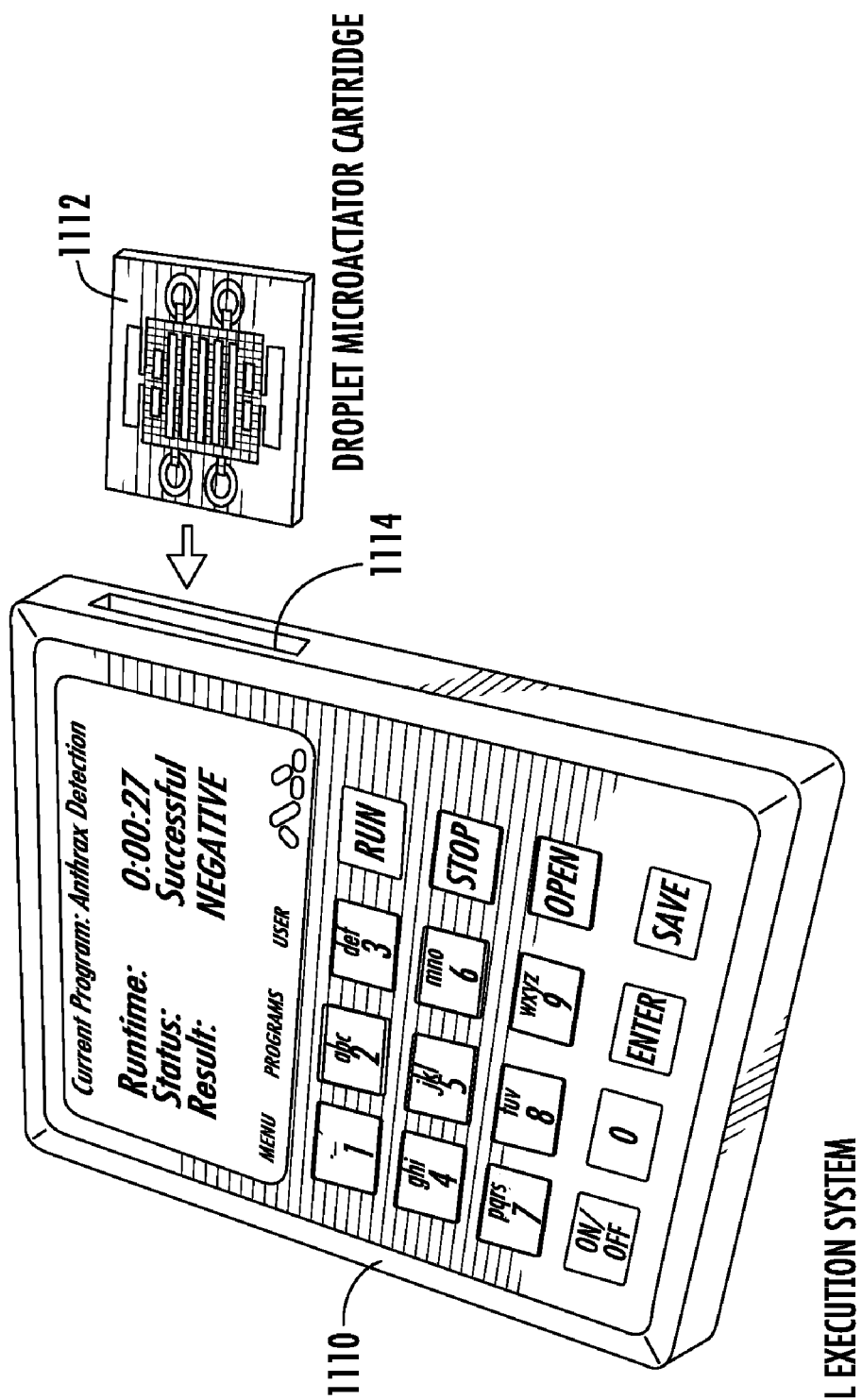
FIG. 11 is an illustration of a portable handheld analyzer in accordance with an embodiment of the present invention.

The invention also can provide a protocol execution system. The protocol execution system includes protocol execution software programmed to facilitate execution of a set of software instructions for controlling droplet operations on the droplet microactuator and other functions of a droplet microactuator and related hardware. The protocol execution system provides the ability to execute protocols on a free-standing system, typically a portable or handheld system, e.g., as illustrated in FIGS. 5A and 5B as discussed hereinabove. FIG. 11 illustrates a further conceptual handheld system 1110 wherein a droplet microactuator cartridge 1112 can be inserted into a slot 1114 for analysis. Subroutines defining protocols for execution on the protocol execution system may be prepared using a programming language, described above, with or without the use of the programming system.

The protocol execution system is configured to control the droplet microactuator and may also control associated components such as detectors, heaters, latch switches, etc. Pre-programmed instructions may be loaded into the controller which controls the system and which may also control associated components.

The protocol execution system may include various components for permitting a user to provide input to and obtain output from the processor. The human-machine interface may be facilitated using a HMI board, as illustrated in FIG. 9. The HMI board typically includes a controller module and various electronic components, such as buses and ports for electronically coupling input and output devices with the processor.

8.1.3 Detectors

The system may include one or more on-chip and/or off-chip detectors or mechanisms for analyzing droplets or droplet attributes. For example, the droplet microactuator may include one or more detection methods such as amperometry, potentiometry, conductometry, absorbance, chemiluminescence, fluorescence, and/or temperature.

Figure 12:
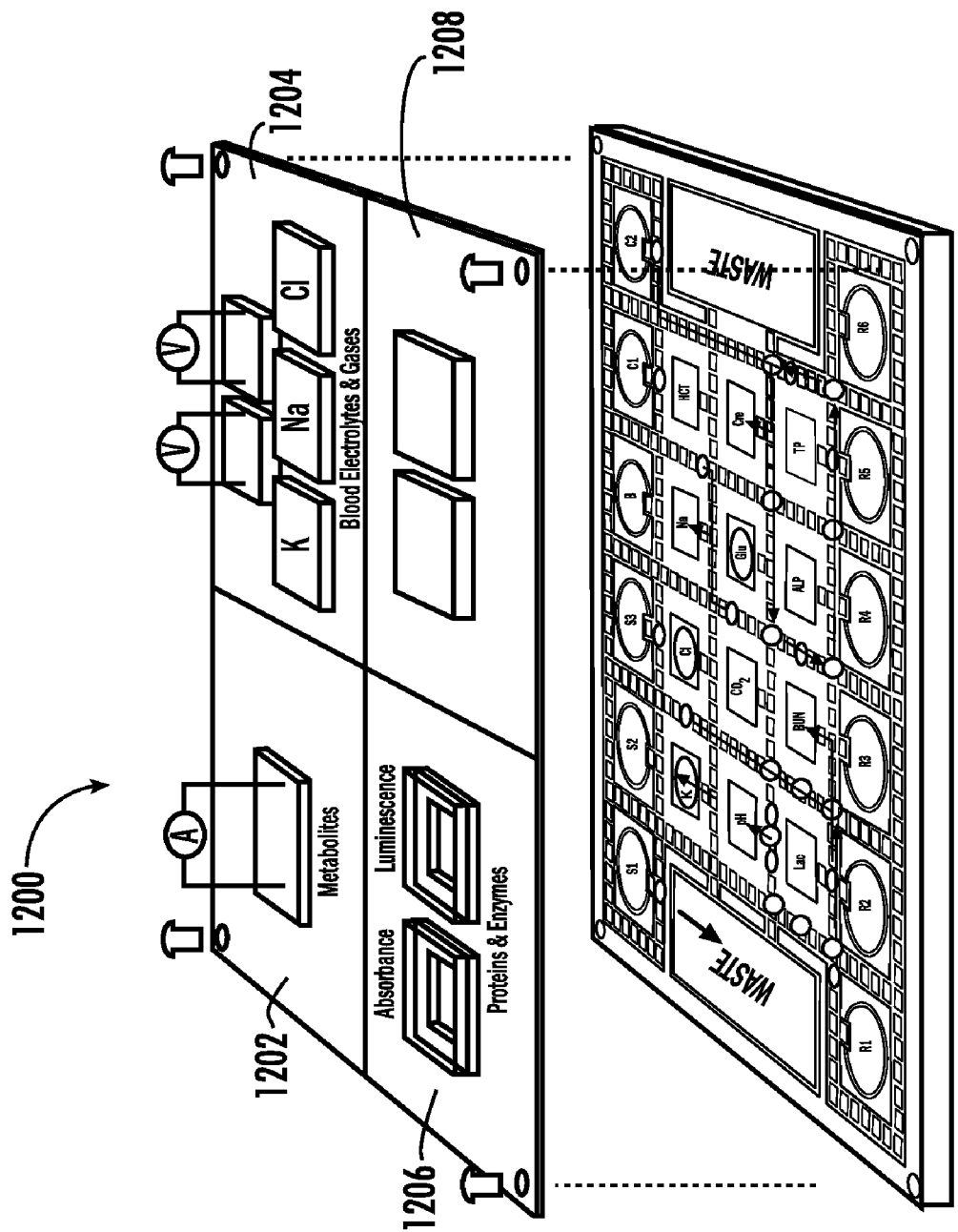
FIG. 12 is a perspective view of a biological fluid analyzer in accordance with an embodiment of the present invention.

The droplet manipulation module and the detection module may in some embodiments be decoupled by building them on separate substrates. Alternatively, the droplet microactuator may incorporate detection components. FIG. 12 shows detection components integrated with a droplet microactuator, the embodiment illustrating a biological fluid analyzer 1200. In this embodiment, various components or modules may be provided for conducting biological fluid analysis, such as, for example, detection of metabolites (e.g., glucose, lactate, blood urea nitrogen, and creatinine), electrolytes (e.g., $K^+$, $Cl^-$, and $Na^+$), proteins, and enzymes. These various modules may include amperometric module 1202, potentiometric module 1204, optical module 1206, and conductometric module 1208. In either case (separate substrates or incorporated), the droplet detection device(s) are preferably electronically coupled to and controlled, at least in part, by the controller.

The detection capabilities may thus be provided as a component of a detector controller board, as illustrated in FIGS. 7 and 8, discussed hereinabove. The detector controller board can include one or more detectors. The board may include various signal amplifiers, such as a photomultiplier tube, for amplifying signal received from a droplet. The detector controller board may include control elements for other off-chip components of the detection protocol, such as control of motors for moving components of the system. For example, in one embodiment, the detector controller board includes a servo motor controller for controlling a servo motor that moves a magnetic field source into and out of proximity with the droplet microactuator, thereby applying/removing the magnetic field to/from the droplet microactuator. The detector controller board may also include power supply elements and communication elements, including without limitation, elements required to electronically couple the detector components or control components of the board to the processor.

Thus, for example, a system of the invention may include one or more of the following, on-chip or off-chip: amperometry module arranged to measure current flowing through a droplet; potentiometry module including a measuring and a reference electrode arranged to measure equilibrium electrode potential of a droplet; conductometry module arranged to measure conductivity of a droplet; absorbance module arranged to measure energy or light absorbance of a droplet; chemiluminescence module designed to measure light emission by chemical species in a droplet, such as fluorescence. Off chip detection modules may, for example, be provided in a cartridge that comprises the chip and/or in an analyzer to which the cartridge or chip may be coupled.

Preferred detection methods are absorbance, electrochemical, fluorescence, and chemiluminescence. In one embodiment, two or more of these methods are accomplished by a single system. In another embodiment, the system includes one detection module, but the system is programmed to conduct more than one test using the module. In this embodiment, processed sample droplets requiring testing are sequentially moved into position for testing. Thus, multiple samples are multiplexed over a detection spot where a single detector is used. Alternatively, the system may contain multiple different detection modules each allowing droplets to be sequentially moved into the position of one of the detection modules.

Figure 13:
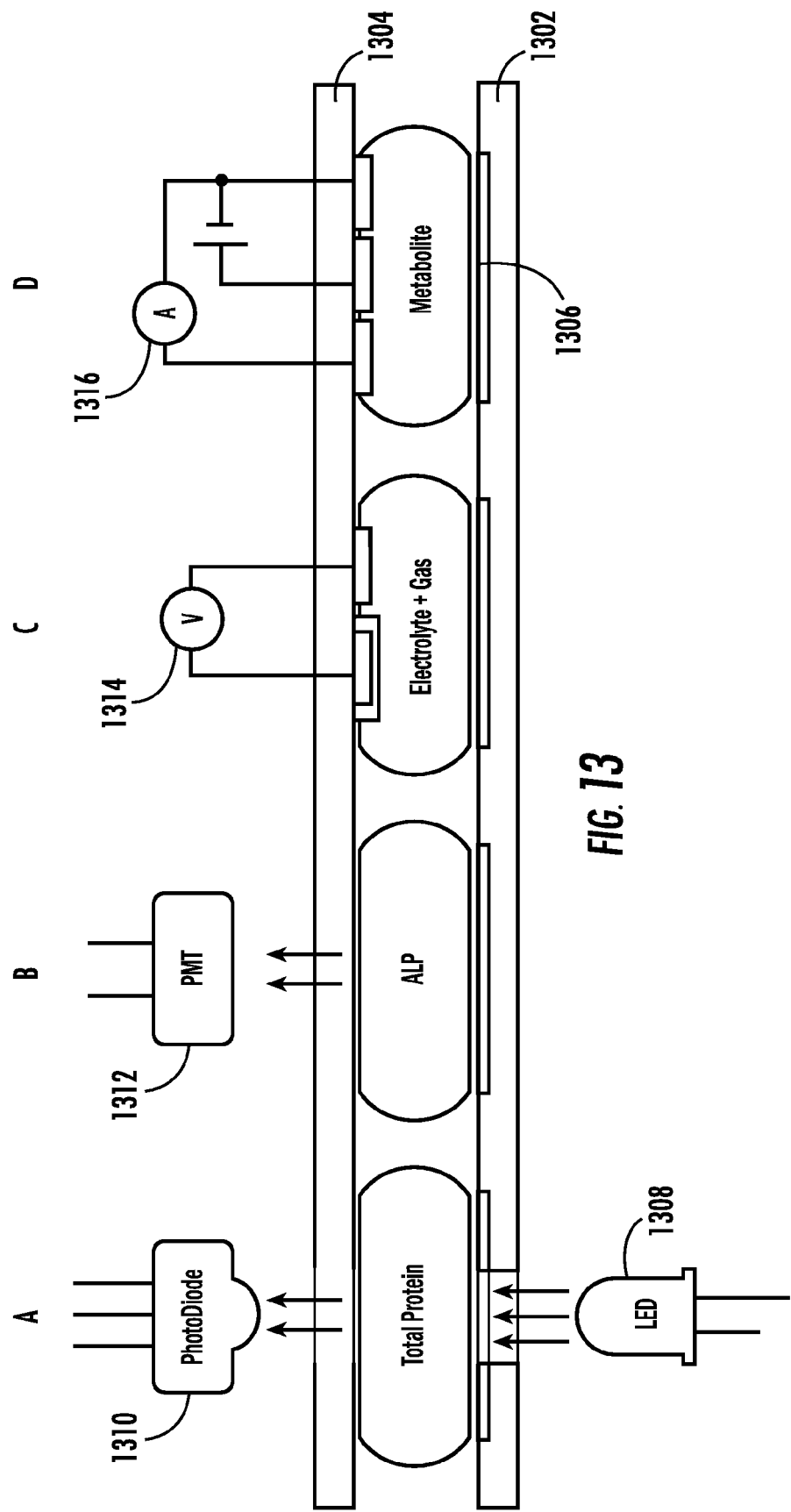
FIGS. 13A-13D are side profile views illustrating various droplet microactuator sensor element configurations in accordance with various embodiments of the present invention.

Illustrative examples of sensor configurations are provided in FIGS. 13A-13D wherein the sensors may be provided in association with a bottom plate 1302, a top plate 1304, and electrodes 1306. FIG. 13A illustrates an optical sensor which may include use of a setup including an LED 1308 and a photodiode 1310 for monitoring absorbance. FIG. 13B illustrates a luminometric sensor which may include use of a photomultiplier tube (PMT) 1312. FIG. 13C illustrates a potentiometric sensor 1314 which typically functions based on the measurement of a potential under no current flow. FIG. 13D illustrates an amperometric sensor 1316 which typically functions by the production of a current when a potential is applied between two electrodes.

Other suitable detectors and sensor configurations are described in International Patent Application No. PCT/US 06/47486, entitled "Droplet-Based Biochemistry," filed Dec. 11, 2006, the entire disclosure of which is incorporated herein by reference.

8.1.4 Other Methods

This aspect of the present invention also includes a method in which components of a bench-top system are offered to or provided to a customer in exchange for consideration. In one embodiment, the components offered to or provided to the customer do not include the PC. The software of the invention may be provided to the user on a storage medium or made available for download via a network, such as the Internet. The user may obtain other components of the system, couple the components to a PC, load the software on a PC, and thereby assemble the system of the invention. The system may also be provided with access to an online source of protocols which may be downloaded and executed on the system. The body of available protocols may be routinely updated or supplemented. Advertising may be associated with the online protocols. The online protocols may be associated with a scoring system, permitting users to score the effectiveness of various protocols and/or post user comments so that other users may use scores and/or comments to assist in the selection of appropriate protocols.

The invention includes a method in which a bench-top system is used to generate code for executing a protocol. Code can be uploaded into a separate system, such as a portable or handheld system, which is offered to or provided to a customer in exchange for consideration. The user may use the system for executing the protocol.

The invention also includes a method in which programming and/or system control is effectuated remotely via a network, such as a telephone system or the Internet. Thus, for example, a system may be sold to a user, a programmer may connect to the system via a user interface displayed via the Internet to control the system, create programs using the system, load programs on the system, and/or repair programs on the system. As another example, the invention includes a process whereby a remote user accesses a droplet microactuator via a network and performs one or more droplet manipulations on the system.

8.1.5 Systems Summary

As will be appreciated by one of skill in the art, the present invention may be embodied as a method, system, or computer program product. Accordingly, various aspects of the present invention may take the form of entirely hardware embodiments, entirely software embodiments (including firmware, resident software, micro-code, etc.), or embodiments combining software and hardware aspects that may all generally be referred to herein as a "circuit," "module" or "system." Furthermore, the present invention may take the form of a computer program product on a computer-usable storage medium having computer-usable program code embodied in the medium.

Any suitable computer useable medium may be utilized for software aspects of the invention. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include some or all of the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission medium such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device.

Computer program code for carrying out operations of the present invention may be written in an object oriented programming language such as Java, Smalltalk, C++ or the like. However, the computer program code for carrying out operations of the present invention may also be written in conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network (LAN) or a wide area network (WAN), or the connection may be made to an external computer (for example, through the Internet using an Internet Service Provider).

The present invention is described with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

8.2 Portable Analyzer

The invention also provides a portable sample analyzer system and related devices and methods. As described hereinabove, FIGS. 5A, 5B, and 11 illustrate two embodiments of this aspect of the invention. In general, the portable system includes an analyzer component and a cartridge component which is configured to be electronically coupled, and typically also physically coupled, to the analyzer component. In FIG. 11, the schematic portrays an analyzer and a cartridge configured so that insertion into the analyzer physically and electronically couples to cartridge to the analyzer. In a typical embodiment, the analyzer component includes a controller or processor for directing operations of various components of the system, a means for coupling the analyzer to cartridge, and any of a variety of input or output components. The cartridge generally includes the droplet microactuator and means for coupling the droplet microactuator to the analyzer. The droplet microactuator component of the cartridge generally includes droplet transport pathways or networks, reagent and/or sample loading means, reagent and/or sample storage reservoirs, and other droplet processing components, such as droplet dispensing components, droplet heating/cooling components, and/or components for subjecting droplets to magnetic fields. The analyzer and/or the cartridge may also include various detector subsystems for detecting output on or from the droplet microactuator. Sample preparation and loading components may also be included as aspects of the analyzer and/or cartridge. Among other things, the system is programmed to control the components of the system to conduct, measure the results of, and communicate information relating to various assays.

As discussed hereinabove, the portable analyzer system typically includes an analyzer component and a cartridge component which is electronically coupled, and typically also physically coupled, to the analyzer component. The analyzer component typically includes a controller which can be programmed to control various aspects of the system (though in some embodiments, the processor controlling the system can be located elsewhere, such as on a computer electronically coupled to the system). The cartridge includes means for electronically coupling various aspects of the cartridge with the controller. In particular, when the cartridge is coupled to the analyzer, the droplet microactuator component of the cartridge is coupled to and capable of being controlled by the controller.

Various input means, such as keyboards, switches and touch screens, and various output means, such as display screens, output ports, and wireless transmitting devices, may also be included in electronic communication with the controller. As described above with reference to Section 8.1.1.5, systems can be programmed to execute a wide variety of protocols involving any number of droplet manipulations.

The controller generally includes a microcontroller, various other electronic components, and associated software. The controller may be set up to receive instructions from input devices and/or to store its own test protocols and other programs. The controller may be set up to receive programs or real-time feedback from the cartridge in order to control operations on the cartridge, such as dispensing or transporting droplets as part of a test protocol. The controller may also provide instructions to the other elements of the analyzer, such as activating or deactivating the detectors.

The controller typically includes a microprocessor for performing calculations related to the derivations and interpretation of results from the tests. Such calculations may involve stored mathematical relationships or numerical constants and may include inputs from the user interface. A droplet is held in place or moved by the activation of electrodes controlled by the controller. In a related embodiment, the controller is electronically coupled to and receives from a separate computer instructions which control various elements of the analyzer.

The system can be programmed to enable users to input instructions for the execution of protocols. Existing protocols may be monitored and adjusted according to user requirements. Complex protocols can be implemented in which the outcome of one or more steps determines the selection of one or more subsequent steps. For example, a droplet in which a certain measured result is positive may be transported for further processing, while a droplet in which a result is negative may be discarded, or vice versa.

Flexibility of operations in the systems of the invention is much greater, for example, than the flexibility of robotic systems, which would require a massive assembly of robotics, a huge facility, and thousands of times the amount of reagents to achieve anything near the massively parallel operations that are enabled by the droplet microactuator. Nevertheless, in some embodiments, robotics may be useful for droplet microactuator or cartridge placement, reagent loading, placement of detectors for external measurements of on-chip phenomena, and the like.

In one embodiment, the portable system generally includes an analyzer component and a cartridge component. In general, a sample, e.g., a liquid sample, may be subjected to preparation during or after sample extraction or collection. This sample is then loaded at the sample interface to the sample loading subsystem on the cartridge. The system may subdivide the sample into multiple sample droplets, e.g., for preparation and execution of multiple tests. Each sample droplet may be further subdivided and/or may be subjected to various types of sample preparation on the cartridge.

Generally each sub-sample droplet will be subjected to various processing steps and/or combined with one or more reagents in accordance with a test protocol. The test protocol may be modified during the test as intermediate results become available.

The output of the test of each sub-sample is an optical or electrical signal. This signal is transmitted across the electronic or optical interface to the electrical and/or optical detectors on the analyzer. The sample loading, reagent distribution, sample preparation, and test execution are actively controlled by the controller on the analyzer across the electronic interface. There may also be feedback from the cartridge to the controller regarding the condition of the cartridge or the status of some task occurring on the cartridge.

Figure 14:
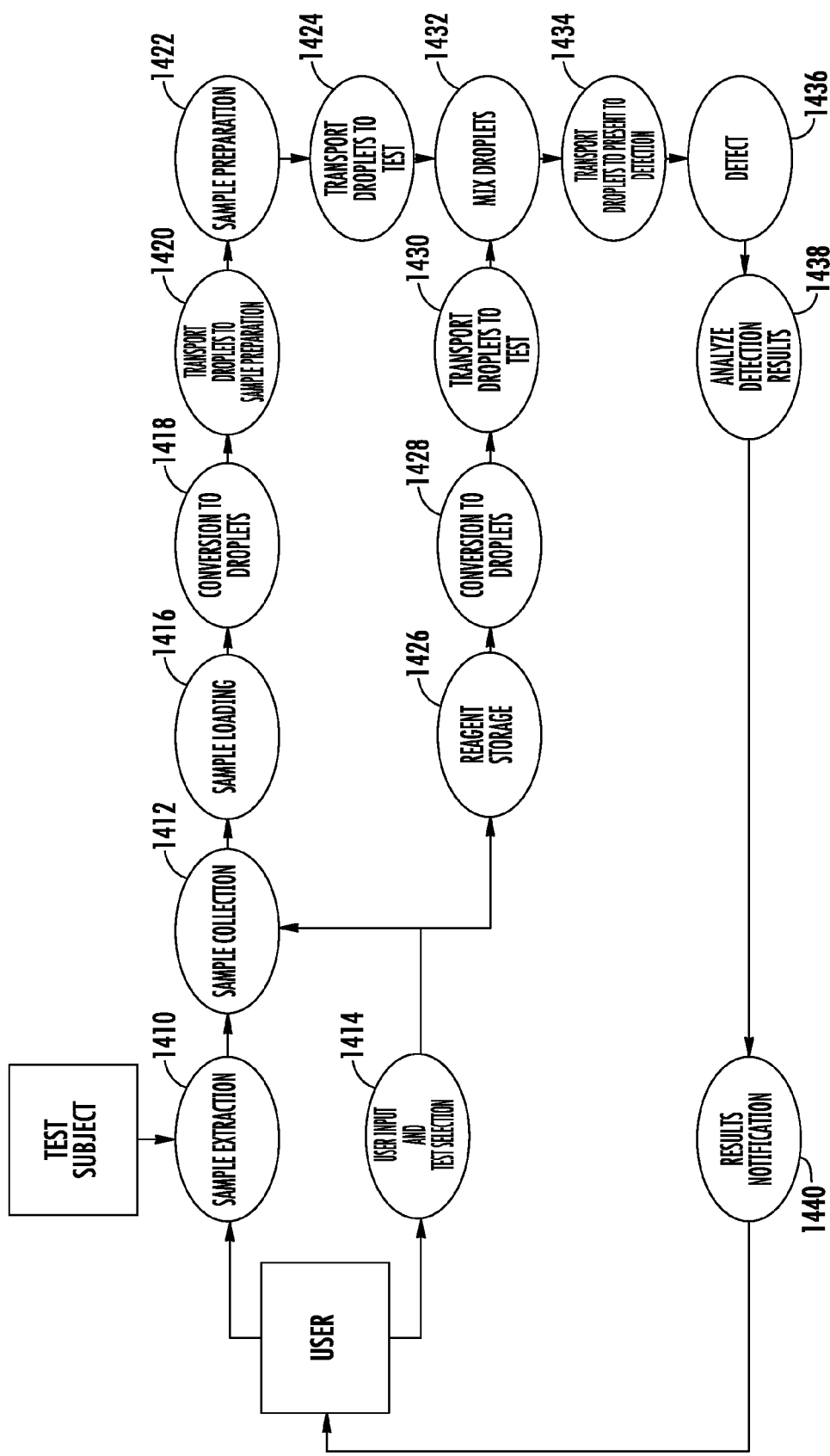
FIG. 14 is a block diagram illustrating functional steps of using a portable system in accordance with an embodiment of the present invention.

Step-by-step function of one embodiment of the portable system of the present invention is illustrated in FIG. 14. It will be appreciated that the steps are not necessarily performed in the order indicated. In steps 1410 and 1412, a sample is extracted from the test subject and the sample is collected. In step 1414, the system is instructed by the user to perform a specific test protocol using droplet operations. For example, a user may select tests to be performed from a menu of tests on the analyzer or the cartridge may provide input to the analyzer signaling the analyzer to run certain pre-loaded protocols. The sample is loaded onto the cartridge in step 1416. The cartridge provides a means for further loading the fluid onto the surface of the droplet microactuator for processing. Bulk fluids are converted on-chip into discrete droplets and transported using droplet operations to sample preparation in steps 1418 and 1420. Sample preparation is performed in step 1422 and the droplets are transported in step 1424. Stored reagents are delivered to the test in the same manner—bulk fluids are converted into discrete droplets and then the appropriate quantity of droplets is transported using droplet operations to the test. Reagent storage, conversion to droplets, and transport are conducted in steps 1426, 1428, and 1430. The sample droplets and reagent droplets transported using droplet operations in steps 1424 and 1430 are mixed in step 1432. Droplet operations are managed by the controller on the analyzer in a step-by-step fashion. In step 1434, the combined sample and reagent mix, or some portion thereof, is then transported into contact with an electronic sensor, such as an electrochemical detector, or is presented through a "window" in the cartridge to an optical detector that is integrated into the cartridge or is situated on the analyzer in such a way that the optical signal can be observed.

In the preferred embodiment the analyzer remains "dry" as sample and reagents are confined to the cartridge. In an alternative embodiment the system may use multiple cartridges to perform the test. For example, a reagent cartridge containing sufficient reagent to perform many tests may communicate with a single-use test cartridge within the analyzer. In this case the analyzer may need to be "wet" to facilitate the plumbing together of the multiple cartridges. Upon completion of the detection step 1436, the droplet can be transported to a waste reservoir and the detection results can be analyzed in step 1438. There may be some feedback between the detector and controller, such that once adequate results are captured the test can be terminated. In step 1440, the user is notified of the results of the test on a display or through some other communications means and the test subject is informed.

8.2.1 Analyzer

As discussed hereinabove, the analyzer generally includes 1) a means for user input at the user interface; 2) a hardware and software controller for the electrical microactuation of the droplets and other actions required to load the sample, prepare the sample, deliver reagents, and execute the test; 3) a means or multiple means for detection of results; 4) a means of performing any necessary calculations; and 5) a means for notification and display of results through the user interface.

The user input means may, for example, include buttons, a display screen, a touch screen, and ports coupling the analyzer to a computer control. A single cartridge of the invention has the capability of being designed or programmed to perform many different tests. Unlike existing systems, in the preferred embodiment of the invention, the test protocol may be modified by the user, e.g., to select specific tests. The user may also enter specific calibration or other analytical information, e.g., that aids sample loading, sample preparation, droplet control, detection, or analysis of data. For example, the user may enter a level of confidence required, and system can be programmed to repeat the test until that confidence level is achieved. User input may, for example, be accomplished by pressing buttons, by addressing variable inputs available on a software-driven touch screen, or through an interface with a software program on a computer, memory card, or other input. User inputs may also be delivered through the electronic or optical interface from the cartridge. The cartridge may contain information encoded in a memory droplet microactuator or other means to provide calibration data, cartridge identification, production lot numbers, expiration date or other information.

The system can also include an output means for reporting test results. For example, results may be reported on a visual display, may be sent to a printer, or may be output to a computer for display, transmission, or further analysis. The invention may include a means for wireless transmission of data as well. The same device used for user input may be used for results notification.

8.2.2 Cartridge and Droplet Microactuator

A cartridge can be provided that interfaces with the analyzer through an electronic interface, an optical interface, or both and generally includes some or all of the following: 1) a means for loading reagent and/or sample onto the cartridge; 2) a means for loading and/or storing reagent and/or sample materials; 3) a means for preparing samples; and 4) a droplet microactuator for performing droplet operations, such as transporting samples, sub-samples, and reagents and performing tests within the cartridge and/or performing various processing steps, such as dilutions, mixing, heating and incubation. Ideally, the cartridge is physically fitted to the analyzer in a manner designed to align relevant electronic and/or optical interfaces. The cartridge may also include a memory device for storing information or instructions, such as information and/or instructions about test type, test protocol steps, and calibration data. Cartridges are discussed in further detail hereinbelow with reference to Section 8.3.3.

8.2.3 Detector Subsystems

The analyzer and/or cartridge of the present invention may include various detector subsystems. A detector subsystem may include one or more detectors and associated electronics and mechanical elements. A droplet, which is the result of the planned preparation of a sample and/or mixing with a reagent or reagents in a planned protocol, has a detectable characteristic. The droplet can then be transported into the sensory range of or into contact with a detector. Since the droplet-based technology provides an accurate, measurable, known volume, the detector output can be used to provide a quantitative measure of the presence or condition of the target analyte. The droplet to be measured, however, may be quite small, preferably from about 1 fL to about 1 mL, more preferably from about 0.1 nL to about 10 μL, still more preferably from about 1 nL to about 1000 nL so the means of detection must be adapted to properly detect the desired characteristic despite the natural reduction in signal because of the low volume.

Several methods of detection can be incorporated into the analyzer or cartridge. In one embodiment the sample, or the results of a sample preparation or assay step, can be presented into contact with electrochemical detectors. The cartridge brings discrete droplets into contact with individual sensors. The droplet-based microfluidics of the invention provide fixed and discrete volume for this electrochemical analysis, which enables highly accurate test results. Other techniques present a "pool" of sample and reagent to an array of detectors, and the chemical reactions required to make each sensor work can interfere with each other. In the subject invention, each electrochemical reaction typically takes place in its own microenvironment.

In another embodiment of the detection subsystem of the invention the chemical assay is designed to produce a fluorescent signal. The reaction takes place in the presence of an optical window and/or the products or some portion of the reaction products are transported to the optical window. The advantage of the invention relative to fluorescent detection relates to the discrete nature of the droplet-based system, wherein very accurate volumes of sample and reagent can be mixed, and the level of fluorescent output is more carefully controlled.

In addition, many samples can be presented to a single detector, as droplets can be cycled in view of the detector on a schedule designed to measure fluorescent output as a function of time. Thus a single detector can be used to simultaneously follow multiple reactions over time. In other systems with less complex liquid handling systems separate detectors must be used if simultaneous results are required. In one embodiment, illustrated in FIG. 5B, the invention makes use of a photomultiplier tube mounted on the analyzer portion of the system for detecting and measuring weak light signals emitted from the droplet microactuator.

Similarly, in another embodiment, the chemical assay is designed to produce a luminescent output. A luminescence detector is placed opposite the same or another optical window. The reaction takes place opposite the optical window and/or the products or some portion of the reaction products are transported to the optical window. The luminescence detection approach is typically a more sensitive detection technique. Otherwise, the technique benefits from advantages analogous to those described above for fluorescence detection.

In another embodiment the concentration of a target analyte is known to absorb light of a particular wavelength as a function of concentration. The droplet, once prepared for analysis, is placed in the path of light, and a photodetector is used to measure the change in light output.

These detection methods can be used in combination to conduct multiple assays simultaneously using the same or different detectors. A single assay can also be measured using multiple detection techniques to enhance confidence in the output.

8.2.4 Assays

The system of the invention may be programmed to execute various assay protocols. Multi-step enzymatic assays, for example, involve the sequential addition of materials to the sample. The end result is typically a color change, luminescent or output, for example, which can be detected by optical means.

The system of the invention may be programmed to execute immunoassays. Suitable immunoassay approaches are described in International Patent Application No. PCT/US 06/47486, entitled "Droplet-Based Biochemistry," filed on Dec. 11, 2006, the entire disclosure of which is incorporated herein by reference. An antibody is stored as a reagent on the cartridge, and brought into contact with the sample material. The antibody binds to the analyte or biological material of interest from the sample. The antibody is typically anchored to the surface of the transport means by chemical or magnetic means, e.g., permanently or by activating or presenting a magnetic field, while the remaining sample materials are removed. Additional reagents may then be introduced to produce or attach a luminescent, fluorescent, or otherwise detectable output that is proportional to the quantity of analyte or biological material captured by the antibody. Multiple antibodies may be used, and a competitive format for the assay may be implemented as well, wherein a specified amount of the analyte tagged with a fluorescent or luminescent marker is present as a reagent and the analyte in the sample must compete for antibody attachment sites. In this instance the greater the detected signal, the lower the quantity of detected analyte.

In another embodiment, polymerase chain reaction (PCR) is implemented on the cartridge to amplify DNA present in the sample. Suitable PCR approaches are described in International Patent Application No. PCT/US 06/47486, entitled "Droplet-Based Biochemistry," filed on Dec. 11, 2006, the entire disclosure of which is incorporated herein by reference. In general, the appropriate reagents are added and the sample/reagent mixture is thermocycled at closely controlled temperatures to amplify the DNA. Thermal cycling may be accomplished using one or more heaters by changing the temperature of the heater, or in a more preferred embodiment, transporting the droplet using droplet operations into proximity with and away from a single heater or into proximity with and away from multiple heaters set at different temperatures. Amplification can be detected between each cycle, or every few cycles, to measure progress. Amplification can be stopped once sufficient progress has been attained. In some embodiments, thermal cycling is attained in the absence of thermal cycling a heater.

In another embodiment DNA sequencing is preformed on the cartridge by capture of the genetic material on a surface, such as beads or a surface of the chip. After addition of the appropriate reagents, sequential addition of bases is performed. A fluorescent or luminescent output may be detected when the correct base is incorporated.

In general, the maximization of signal output from the biochemical process involves selecting the best type of assay for detecting a particular analyte, maximizing the useable signal on a per volume basis for that assay type, ascertaining that consistent results can be obtained in the relevant concentration range, and minimizing the signal attenuation or other interference with the signal through proper sample preparation or further assay steps.

8.3 Droplet Microactuator Architecture and Operation

The various aspects of the present invention discussed hereinabove generally include a droplet microactuator controlled by a processor. For example, the processor may, among other things, be programmed to control droplet manipulations on a droplet microactuator. A wide variety of droplet microactuator configurations are possible. Examples of components which may be configured into a droplet microactuator of the invention include various filler fluids which may be loaded on the droplet microactuator; fluid loading mechanisms for introducing filler fluid, sample and/or reagents onto the droplet microactuator; various reservoirs, such as input reservoirs and/or processing reservoirs; droplet dispensing mechanisms; means for controlling temperature of the droplet microactuator, filler fluid, and/or a droplet on a droplet microactuator; and magnetic field generating components for manipulating magnetically responsive beads on a droplet microactuator. This section discusses these and other aspects of the droplet microactuator and their use in the systems of the invention.

8.3.1 Droplet Microactuator

The various aspects discussed hereinabove can make use of a droplet microactuator, sometimes referred to herein as a chip. The droplet microactuator can include a substrate with one or more electrodes arranged for conducting one or more droplet operations. In some embodiments, the droplet microactuator can include one or more arrays, paths or networks of such electrodes. A variety of electrical properties may be employed to effect droplet operations. Examples include electrowetting and electrophoresis.

In one embodiment, the droplet microactuator includes two or more electrodes associated with a substrate, and includes a means for permitting activation/deactivation of the electrodes. For example, the electrodes may be electronically coupled to and controlled by a set of manual switches and/or a controller. The droplet microactuator is thus capable of effecting droplet operations, such as dispensing, splitting, transporting, merging, mixing, agitating, and the like. Droplet manipulation is, in one embodiment, accomplished using electric field mediated actuation. Electrodes will be electronically coupled to a means for controlling electrical connections to the droplet microactuator.

The basic droplet microactuator includes a substrate including a path or array of electrodes. In some embodiments, the droplet microactuator includes two parallel substrates separated by a gap and an array of electrodes on one or both substrates. One or both of the substrates may be a plate. One or both substrates may be fabricated using PCB, glass, and or semiconductor materials as the substrate. Where the substrate is PCB, the following materials are examples of suitable materials: Mitsui BN-300; Arlon 11N; Nelco N4000-6 and N5000-30/32; Isola FR406, especially IS620; fluoropolymer family (suitable for fluorescence detection since it has low background fluorescence); and the polyimide family. Various materials are also suitable for use as the dielectric component of the substrate. Examples include: vapor deposited dielectric, such as parylene C (especially on Glass), and parylene N; Teflon AF; Cytop; and soldermasks, such as liquid photoimageable soldermasks (e.g., on PCB) like Taiyo PSR4000 series, Taiyo PSR AUS series (good thermal characteristics for applications involving thermal control), and Probimer 8165 (good thermal characteristics for applications involving thermal control); dry film soldermask, such as those in the Dupont Vacrel family; and film dielectrics, such as polyimide film (Kapton), polyethylene, and fluoropolymers like FEP, PTFE. Some or all of the substrate may also include a hydrophobic coating. Suitable examples include Teflon AF; Cytop; coatings in the Fluoropel family; silane coatings; fluorosilane coatings; and 3M Novec electronic coatings.

Where the droplet microactuator includes two plates, droplets may be interposed in the space between the plates. Space surrounding the droplets typically includes a filler fluid. The droplet microactuator can conduct droplet operations using a wide variety of fluid droplets, though conductive fluids are preferred. Filler fluids are discussed in more detail hereinbelow with reference to Section 8.3.4.

Surfaces of the droplet microactuator are typically coated with a hydrophobic coating. For applications involving thermal cycling, a hydrophobic coating should be selected that is resistant to thermal stress during prolonged thermal cycling operation. Examples of suitable thermal resistant materials include soldermasks such as Probimer® 8165 which has been developed for use in the automotive industry and has excellent thermal shock resistance, and PCB board materials such as Mitsui BN-300 which is resistant to high temperature and warpage.

Droplet transport occurs along a path or network of control electrodes. The array or path includes electrical connections for electrically coupling electrodes to external circuitry. The array or path may also include electrical connections for electrically coupling certain electrodes together. The electrodes can be controlled via the external circuitry by a processor. Droplet operations may be effected by supplying voltage to the electrodes. While the preferred voltage varies depending on the thickness of the dielectric, for a dielectric constant in the range of 2-100 and thickness in the range of 1 nm to 10 mm, the preferred energy per unit area limits are in the range of about 300 microjoule/sq meter to about 300000 microjoule/sq meter. The preferred activation voltage is in the range of about 1 mV to about 50 kV, or about 1V to about 10 kV, or about 5V to about 1000V, or about 10V to about 300V.

Typically, the electrodes are fired via a voltage relay. The droplet microactuator operates by direct manipulation of discrete droplets, e.g., using electrical fields. For example, a droplet adjacent to an energized electrode with surrounding electrodes grounded will transport to align itself with the energized electrode, i.e., the droplet will be transported to the position of that electrode. A series of successive transfers will transport droplets along the path or network of control electrodes. In addition to transport, other operations including merging, splitting, mixing and dispensing of droplets can be accomplished in the same manner by varying the patterns of voltage activation.

It should be noted that electrodes can be activated in a variety of ways. For example, an electrode can be activated by applying a DC potential. Similarly, an electrode can be activated by applying an AC potential, so that the activated electrode has an AC potential and an unactivated electrode has a ground or other reference potential. In another aspect, the potential may be applied by repeatedly activating an electrode and then inverting it. An AC mode can be effected by using software to rapidly switch between polarities of the outputs.

In some embodiments the invention employs droplet operation structures and techniques described in U.S. Pat. No. 6,911,132, entitled "Apparatus for Manipulating Droplets by Electrowetting-Based Techniques," issued on Jun. 28, 2005 to Pamula et al.; U.S. patent application Ser. No. 11/343,284, entitled "Apparatuses and Methods for Manipulating Droplets on a Printed Circuit Board," filed on Jan. 30, 2006; U.S. Pat. Nos. 6,773,566, entitled "Electrostatic Actuators for Microfluidics and Methods for Using Same," issued on Aug. 10, 2004 and 6,565,727, entitled "Actuators for Microfluidics Without Moving Parts," issued on Jan. 24, 2000, both to Shenderov et al.; U.S. Patent Publication No. 20060254933, entitled "Device for transporting liquid and system for analyzing" published on Nov. 16, 2006 to Adachi et al.; International Patent Application No. PCT/US 06/47486, entitled "Droplet-Based Biochemistry," filed on Dec. 11, 2006; and International Patent Application No. PCT/US 06/47481, entitled "Droplet-Based Pyrosequencing," filed on Dec. 11, 2006, the disclosures of which are incorporated herein by reference for their teachings concerning structures and techniques for conducting droplet operations.

Droplet operations can be rapid, typically involving average linear velocities ranging from about 0.01 cm/s to about 100 cm/s, or from about 0.1 cm/s to about 10 cm/s, more preferably from about 0.5 cm/s to about 1.5 cm/s. Moreover, droplets may typically be manipulated at a frequency of manipulation ranging from about 1 Hz to about 100 KHz, preferably from about 10 Hz to about 10 KHz, more preferably from about 25 Hz to about 100 Hz. In addition to being rapid, droplet manipulations using the droplet microactuator are also highly precise, and multiple droplets can be independently and simultaneously manipulated on a single droplet microactuator.

Discrete droplet operations obviate the necessity for continuous-flow architecture and all the various disadvantages that accompany such an architecture. For example, near 100% utilization of sample and reagent is possible, since no fluid is wasted in priming channels or filling reservoirs. Further, as noted above, droplet movement can be extremely rapid. The droplet microactuator may in some cases be supplemented by continuous flow components and such combination approaches involving discrete droplet operations and continuous flow elements are within the scope of the invention. Continuous flow components may be controlled by the controller. Nevertheless, in certain other embodiments, various continuous flow elements are specifically avoided in the droplet microactuator of the invention and/or methods of the invention. For example, in certain embodiments, one or more of the following components is excluded from a droplet microactuator and/or methods of the invention: microchannels; fixed microchannels; networks of microchannels; pumps; external pumps; valves; high-voltage supplies; centrifugal force elements; moving parts.

Electric field mediated actuation also obviates the need for other droplet operations and all the various disadvantages that accompany such techniques. It will be appreciated that the droplet microactuator may nevertheless be complemented or supplemented with other droplet manipulation techniques, such as electrical (e.g., electrostatic actuation, dielectrophoresis), magnetic, thermal (e.g., thermal Marangoni effects, thermocapillary), mechanical (e.g., surface acoustic waves, micropumping, peristaltic), optical (e.g., opto-electrowetting, optical tweezers), and chemical means (e.g., chemical gradients). When these techniques are employed, associated hardware may also be electronically coupled to and controlled by the controller. However, in other embodiments, one or more of these droplet operation techniques is specifically excluded from a droplet microactuator of the invention.

The droplet microactuator can be manufactured in a highly compact form and can be driven using a very small apparatus. For example, droplet microactuator and apparatus may together be as small as several cubic inches in size. The droplet microactuator requires only small amounts of electrical power and can, for example, readily be operated using batteries. The droplet microactuator can perform droplet operations using extremely small droplets. Droplets are typically in the range of from about 1 fL to about 1 mL, more preferably from about 100 pL to about 1 µL, still more preferably from about 10 nL to about 1 µL.

The use of discrete droplets for on-chip processing instead of continuous flows provides several important advantages. Since sample fluid need not be expended for priming of channels or pumps virtually all of the sample fluid can be used for analysis and very small volumes of sample (e.g., less than about 100 µL or less than about 50 µL or less than about 25 µL) can be analyzed. The same advantages apply to the use of reagents where reducing the volume of reagents consumed has the advantage of reducing the cost of the analysis. The use of discrete small-volume droplets also permits a large number of reactions to performed in a small footprint (e.g. greater than 10 per $cm^2$ or greater than 100 per $cm^2$ or greater 1,000 per $cm^2$ or greater than 10,000 per $cm^2$).

Various components of the invention may be included as components of the droplet microactuator. In fact, an entire system of the invention may be provided as an integrated droplet microactuator. In some embodiments, the droplet microactuator includes various sensors and means for electronically coupling the sensors to external circuitry. In other embodiments, the droplet microactuator includes heaters and/or magnetic field generating elements and means for coupling such elements to external circuitry. Further, a droplet microactuator including any one or more of the reagents described herein in a reservoir or in droplet form is also an aspect of the invention.

Optical windows can be patterned in the electrodes to enhance the capability of performing optical detection on the chip. Where the electrode is formed in an opaque material on a transparent substrate, a window in the electrode can be created permit light to pass through the substrate. Alternatively, when the electrode material is transparent, a mask can be created to eliminate stray light. Additionally, the opening can be patterned as a diffraction grating. Adaptive optical windows can be created as well, using a second electrowetting layer. For example, opaque oil (e.g. oil dyed black) can be used with a transparent droplet to create a temporary and movable optical window.

8.3.2 Droplet Microactuator Fabrication

Droplet microactuators can be made using standard microfabrication techniques commonly used to create conductive interconnect structures on microdroplet microactuators and/ or using printed-circuit board (PCB) manufacturing technology. Suitable PCB techniques include those described in U.S. patent application Ser. No. 11/343,284, entitled "Apparatuses and Methods for Manipulating Droplets on a Printed Circuit Board," filed on Jan. 30, 2006, the entire disclosure of which is incorporated herein by reference. These techniques permit the droplet microactuator to be manufactured in bulk at very low cost. Low cost manufacture enables economical production of droplet microactuators, even for use as one-use disposables. Thus, the invention provides a method in which droplet microactuators are supplied to users as components of disposable cartridges for use in systems of the invention.

Designs can also be implemented on glass or silicon using conventional microlithography techniques with the capability of producing much smaller features than are typical in a PCB process. Even, for example, for a 1,572,864-reservoir droplet microactuator with 70 µm reservoir spacing and 3 fL reservoir volume, the minimum required lithographic feature size is ~0.5 µm which is well within the capabilities of conventional microlithographic techniques currently used in the semiconductor industry.

Because the chip can be loaded directly using manual or robotic pipette dispensers and can be analyzed using standard plate reading equipment, it will easily integrate into existing laboratory work flows. This is a significant advantage over other microfluidic approaches which may require adaptation of the assays to continuous-flow format or specialized equipment for sample handling and read-out.

8.3.3 Cartridge

As discussed hereinabove, in some embodiments, the invention includes a cartridge for coupling to the droplet microactuator. It will be appreciated that a cartridge, while not necessary to the operation of the invention, may be convenient in some circumstances. When present, the cartridge may include a means for electrically coupling the path or network of the droplet microactuator to a processor, e.g., a processor of a droplet microactuator system of the invention. In this embodiment, the electrical connection is: electrodes—cartridge—processor, where there may be additional elements between the three. In another embodiment, the cartridge may include means for physically coupling to the droplet microactuator. In this embodiment, the electrical connection may be: electrodes—processor—cartridge. Alternatively, the cartridge may lack electrical components altogether.

When present, the cartridge may include reservoirs for one or more reagents, e.g., pre-loaded reagents. The droplet microactuator may be configured so that a fluid path may be established between the cartridge reservoirs and the interior of the droplet microactuator for flowing reagents, sample and/or filler fluid from the cartridge onto the droplet microactuator. For example, preloaded cartridge reservoirs may be dispensed into the droplet microactuator prior to, during, or after coupling of the cartridge to the analyzer. The cartridge may be sealed, self-contained and/or disposable. It may be supplied with or without a droplet microactuator. Such cartridges can be used to ensure repeatable assay conditions, permit safe handling and disposal of infectious or hazardous material, and/or reduce cross-contamination between runs. The cartridge may, for example, include a machined plastic part. It may be affixed to and provided in combination with the droplet microactuator.

The cartridge materials are selected to provide storage of reagents without degradation or contamination of the reagents. Moreover, they should be selected to provide reliable operation at elevated temperature and to ensure compatibility with the real-time chemistry. They may, for example, include molded plastic components. In some embodiments, sealed, disposable test cartridges enhance operator safety and facilitate safe disposal.

Various components of the droplet microactuator system may be included on the cartridge. For example, the top-plate, which encloses the interior space of the droplet microactuator, may be provided as a component of the cartridge. Various sensors may also be included as components of the cartridge.

8.3.4 Filler Fluid

The droplet microactuator of the invention includes one or more free (i.e., fluid-fluid) interfaces. Examples include a liquid-liquid or liquid-gas interface. Typically, chemistry is performed in the primary (droplet) phase, and the secondary phase serves as a filler fluid separating the droplets from each other. The secondary phase can, for example, be a liquid, gel, and/or a gas. Where the secondary phase includes a liquid, the liquid is sufficiently immiscible with the primary liquid phase to permit the droplet microactuator to conduct one or more droplet operations.

The system may be programmed to provide for multiple introductions or recirculation of one or more filler fluids within the droplet microactuator. A secondary fluid-handling system can be provided to inject and to remove fluid from within the droplet microactuator. Pressure, gravity or other means such as the use of thermal gradients can be used to transport the filler fluid into or out of the droplet microactuator. Such a system can, for example, be used for the following purposes:

(1) To replenish filler fluid lost to evaporation or leakage over time. A slow steady flow or periodic injection of filler fluid can be employed to make up for any loss of filler fluid volume.
(2) To provide "clean" filler fluid either continually or periodically to reduce contamination between droplets. The filler fluid can be cleaned either by completely replacing it or by circulating it through a filter or bed of absorbent material selected to remove contaminants.
(3) To provide a means for transporting droplets to waste. For example, at the end of an assay, droplets can be released and allowed to flow with the filler fluid to the outlet providing a means to "flush" the droplet microactuator. Flushing the droplet microactuator can be performed to reset the status of the droplet microactuator in preparation to perform additional assays.
(4) To exchange the filler fluid when different fluids may be desired for certain steps, for example to replace oil with air to allow drying of droplets, or to replace one oil with a different oil.
(5) To provide a means of controlling the temperature of the droplets by heating or cooling the fluid as it is circulated through the droplet microactuator. The temperature of the filler fluid entering and leaving the droplet microactuator can be directly measured and the temperature and flow rate of the filler fluid can be adjusted to provide optimal temperature control inside the droplet microactuator.

Suitable filler fluids and operations involving the same are described in International Patent Application No. PCT/US 06/47486, entitled "Droplet-Based Biochemistry," filed Dec. 11, 2006, the entire disclosure of which is incorporated herein by reference.

8.3.5 Droplet Microactuator Loading

The droplet microactuator as contemplated herein generally includes one or more input ports for the introduction of one or more filler fluids, reagents and/or samples (e.g., reagents and/or samples for conducting protocols and/or assays as described elsewhere herein) into the droplet microactuator. In some embodiments, samples or reagents are loaded via the input ports using conventional robotics. In one alternative embodiment, droplets of sample or reagent are separated by plugs of oil in a long pre-loaded capillary (e.g., a glass capillary) which when connected to the droplet microactuator allows droplets of sample or reagent to be captured and routed on the droplet microactuator as they are pumped out of the capillary into the input port. Another loading technique involves pre-stamping reagents onto the droplet microactuator and allowing them to dry, e.g., using a high-speed reagent stamping or printing process. Yet another approach involves the use of a direct plate-to-droplet microactuator interface in which the contents of plates, e.g., 1536 or 384 or 96 well plates, are transported onto the droplet microactuator in parallel by using pressure to force the contents through input ports aligned with wells. Loading hardware may in some embodiments be electronically coupled to and controlled by the controller.

The droplet microactuator can be associated with or coupled with a fluidic input module for loading and storage of sample and/or reagent. For example, a basic input module allows samples to be loaded using a pipettor or other device. The system may be programmed to subdivide and dispense input fluid as discrete droplets which can be transported on the control electrodes networks or pathways.

Since the droplet-based microfluidic system of the invention can operate accurately using very small volumes, the system can incorporate a unique sample loading means which translates this small-volume droplet processing capability into the ability to accept much smaller sample volumes, the input sample volume is typically from about 1 mL to about 100 mL, or from about 100 mL to about 1 mL, or from about 1 µL to about 10 µL. This capability is particularly important in instances where only a small sample volume is available (premature infants or small animals, for example) and in instances where the acquisition of a smaller sample is less painful, less invasive, or medically advisable.

The sample loading means of the invention transfers the sample from a loading port on the cartridge into the droplet microactuator so that droplet operations can be managed by the controller. Preferably this step is accomplished without significant loss of sample. Since the cartridge contains a filler fluid, the sample loading also includes a force to overcome the resistance of the filler fluid, i.e., to push the filler fluid out of the way. Once the sample is loaded into the loading port the loading port is capped, and then a pressure, vacuum or other force may be introduced to overcome the resistance of the filler fluid. In one embodiment, the action of inserting the cartridge into the analyzer squeezes a small rubber diaphragm to create a positive pressure. In another embodiment the sample loading is combined with sample preparation by the introduction of a filter between the loading port and the interior of the droplet microactuator, so that, for example, blood cells can be removed from whole blood, and only blood plasma or serum is introduced into the droplet microactuator. In another embodiment several separate samples are loaded onto a single cartridge, and are analyzed separately, so that a single cartridge is not only capable of multiple tests but can perform these tests on multiple samples.

8.3.6 Reservoirs

The droplet microactuator as contemplated herein may include various reservoirs (sometimes referred to herein as "wells"), such as input reservoirs and/or processing reservoirs.

8.3.6.1 Input Reservoirs

The invention can also include a means for storing sample and/or reagent materials. Preferably reagents are loaded on the cartridge in advance of the test and must be stored. Reagents may be physically separated from each other and may be physically separated from the filler fluid by a mechanical barrier. Reservoirs for each reagent are typically affixed to the cartridge. The cartridge reservoir may include a foil or plastic pouch that can be loaded separately before assembly onto the cartridge. The storage of the reagents for extended periods of time may require that the cartridge be kept in a controlled environment. In another embodiment, reagents may be stored off-cartridge, e.g., in storage containers, and introduced onto the chip for dispensing into droplets.

In existing reagent storage devices, once the mechanical barrier is removed (often a foil pouch is pierced) the reagent is pooled with the sample or carrier fluid to conduct a test. In the present invention once the mechanical barrier is removed—or the pouch is pierced—the reagent is made to flow into an on-chip reservoir, a feature of the droplet microactuator designed for this purpose. This on-chip reservoir retains the reagents until such time as their use is required. The appropriate amount of reagent is then dispensed from the reservoir. The precise amount of reagent needed for a test can be dispensed using programmable electronic control. Thus one reservoir of reagent can be used to supply reagent for multiple tests in differing quantities and at different times. In addition, the amount of reagent loaded into the reservoir is less important because reagent can be metered into the reaction by the on-chip reservoir's dispensing device. This approach eliminates the need for accurate foil pouches or cartridge reservoir loading, thus reducing the cost of the device.

In some embodiments, the droplet microactuator includes one or more input reservoirs (also referred to as "loading wells") in fluid communication with one or more input ports, typically in direct fluid communication with the input ports. The input reservoir(s) serve as reservoirs for storage of bulk source material (e.g. reagents or samples) for dispensing droplets (e.g. reagent droplets or sample droplets). Thus, the input reservoir(s) may, for example, serve as sample wells or reagent wells.

The input reservoirs generally include one or more well reservoirs defining an interior space and an opening. The interior space defined by the well walls is at least partially isolated by the well walls from the remainder of the interior of the droplet micro actuator. The reservoir may be adjacent (in any direction, e.g., vertically or laterally) to a port suitable for introduction of fluid from an exterior of the droplet microactuator into the input reservoir. One or more openings in the reservoir walls may be provided to enable fluid communication with the interior volume of the droplet microactuator for dispensing of droplets into this interior volume. The opening (s) may permit fluid to flow or be transported into the interior volume of the droplet micro actuator onto the path or network of electrodes. Input reservoirs may also include one or more vents for permitting displacement of filler fluid from the input reservoir as fluid is introduced into or removed from the well via the port or the opening.

The input reservoirs may further include one or more planar control electrodes in a top or bottom plate adjacent to or within the space defined by the well walls. The planar electrodes can be electronically coupled to and controlled by the controller. In a preferred embodiment, the planar electrode has two or more branches or rays, such that activation of the control electrode during droplet dispensing in the presence of a fluid exerts a "pull" on the fluid in a direction which is generally opposite to the direction of droplet dispensing. In some cases, the shape of the electrode results in a multi-vector pull having a mean vector which has a direction generally opposite to the direction of the droplet being dispensed.

Well walls may, for example, be formed by protrusions from the top or bottom plates, and/or may be formed by deposition of a wall-forming material on a surface of the top or bottom plate. For example, well walls may be formed from a soldermask material or polymeric gasket material deposited and patterned on the surface. In some embodiments a source of continuous or semi-continuous sample or reagent flow is coupled in fluid communication with one or more of the input ports.

It should be noted that while droplet dispensing may be conducted from defined reservoirs, in some embodiments, droplet dispensing is conducted without the use of physically defined reservoirs. Dispensing may proceed from source droplet which is confined during droplet dispensing, e.g., by electrowetting forces or by hydrophilic surfaces.

8.3.6.2 Processing Reservoirs

The droplet microactuator may also include one or more processing wells, areas, or reservoirs. These reservoirs serve as a location for executing various droplet processing steps, such as mixing, heating, incubating, cooling, diluting, titrating, and the like. The droplet microactuator includes one or more paths or networks of control electrodes sufficient to transport droplets from the one or more input ports to the one or more processing reservoirs. In some cases the processing reservoirs are simply components or sections of these paths or networks. In other embodiments, the processing reservoirs are defined processing reservoirs. Such reservoirs may, for example, be structured generally in the same manner as the input reservoirs described above. However, the processing reservoirs are typically not in direct fluid communication with the input ports, i.e., droplet transport along the one or more paths or networks of control electrodes is required add reagent or sample to the processing reservoir(s). In some cases, the processing reservoirs include a path or network of reservoirs therein to permit droplet operations within the processing reservoirs. In addition to typically lacking a direct interface with the exterior of the droplet microactuator, processing reservoirs are typically smaller than input reservoirs, though in some embodiments, input reservoirs may be smaller but serve as an interconnection between the interior of the droplet microactuator and the chip exterior. As a general rule, the target capacity of the loading ports can be a multiple of the number of reservoirs times the unit volume in cases where the liquid is completely loaded.

In one embodiment, the droplet microactuator includes a regular array of processing reservoirs. In one embodiment, the processing reservoir array dimensions conform to standard Society for Biomolecular Screening microplate (multi-well plate) dimensions, such as the dimensions set forth in "ANSI/SBS 1-2004: Microplates—Footprint Dimensions," as updated on Jan. 9, 2004; "ANSI/SBS 2-2004: Microplates—Height Dimensions," as updated on Jan. 9, 2004; "ANSI/SBS 3-2004: Microplates—Bottom Outside Flange Dimensions," as updated on Jan. 9, 2004; and "ANSI/SBS 4-2004: Microplates—Well Positions," as updated on Jan. 9, 2004. The entire disclosure of each of these documents is incorporated herein by reference for its teaching concerning microplate standards. Certain designs may mix microplate standards on a single device. For example, one portion of the droplet microactuator chip may conform to 96-well format for loading of samples, while another portion conforms to 384 or 1536-format for arraying of reactions. Other designs may subdivide the droplet microactuator chip into modules designed to perform different functions where some modules conform to multi-well plate spacing for loading, storing or detection of reagents or reactions while other modules may have structures designed to perform specific operations or procedures.

Larger chips with extremely high levels of throughput and cost savings will be useful in a variety of settings, such as drug discovery applications. In one embodiment, the invention is useful for high-throughput biological assays. For example, the chip can be programmed to execute on-chip dilutions and cell-handling protocols. Scaling of droplet volumes on a fully populated 128 mm×86 mm plate (chip) size at different well pitches can be seen in Table 1.

which has been mixed within a reservoir may be subsequently dispensed from that reservoir in the form of unit-sized droplets for transport to another reservoir, for example, to perform serial dilution assays.

8.3.7 Thermal Control

The droplet microactuator of the invention may include a means for controlling the temperature of the droplet microactuator or a region of the droplet microactuator. Among other things, thermal control is useful for various protocols requiring heating or cooling steps. Examples include amplification protocols requiring thermal cycling and various assays that require incubation steps.

Thermal control may be controlled by the system. The user interface may be provided with an input means for controlling temperature of one or more heaters, such as a dial or a virtual dial. The user interface may show a temperature gradient around a heater, so that appropriate thermal cycling protocols using droplet transport may be developed by the user.

8.3.7.1 Thermal Control Designs

In general, thermal control may be provided in three ways: (1) thermal control of the entire droplet microactuator; (2) thermal control of a region of a droplet microactuator using a heater that is in contact with or in proximity to the controlled region; and (3) thermal control of a region of the droplet microactuator using a heater that is integrated into the droplet microactuator (e.g., in the substrate comprising the path or array of electrodes and/or in a top plate of the droplet microactuator, when present). Combinations of the foregoing approaches are also possible.

In an integrated heater approach, temperature zones can be created and controlled using thermal control systems directly integrated into the droplet microactuator. Temperatures in and around zones can be shown on the user interface. Integration of thermal control through thin-film heating elements fabricated directly on the droplet microactuator is also useful to maximize the speed, throughput and quality of amplification reactions on the droplet microactuator. Due to their small thermal mass, droplets can be thermally cycled extremely

TABLE 1

Scaling of droplet volumes at different well pitches.

| Well Pitch (mm) | Rows | Cols | Total wells | Well volume (nL) | Unit drop diameter (µm) | Plate spacing (µm) | Unit drop volume (nL) | Min. feature (µm) |
|---|---|---|---|---|---|---|---|---|
| 9.00 | 12 | 8 | 96 | 6750 | 1500 | 300 | 675 | 75.0 |
| 4.50 | 24 | 16 | 384 | 844 | 750 | 150 | 84.4 | 37.5 |
| 2.25 | 48 | 32 | 1536 | 105 | 375 | 75.0 | 10.5 | 18.8 |
| 1.13 | 96 | 64 | 6,144 | 13.2 | 188 | 37.5 | 1.32 | 9.38 |
| 0.563 | 192 | 128 | 24,576 | 1.65 | 93.8 | 18.8 | 0.165 | 4.69 |
| 0.281 | 384 | 256 | 98,304 | 0.206 | 46.9 | 9.38 | 0.0206 | 2.34 |
| 0.141 | 768 | 512 | 393,216 | 0.0257 | 23.4 | 4.69 | 0.00257 | 1.17 |
| 0.070 | 1536 | 1024 | 1,572,864 | 0.00322 | 11.7 | 2.34 | 0.000322 | 0.586 |

Further, the number of reservoirs on the droplet microactuator can be much larger than provided for in existing microplate specifications. For example, a droplet microactuator can incorporate greater than 1,000, 5,000, 10,000, 15,000, 20,000, 25,000, 30,000, 35,000, 40,000, 45,000, 50,000, 55,000, 60,000, 65,000, 70,000, 75,000, 80,000, 85,000, 90,000, 95,000, 100,000, 200,000, 300,000, 400,000, 500,000, 600,000, 700,000, 800,000, 900,000, or even 1,000,000 wells on a single plate.

Mixing or dilution ratios can be established programmably by controlling the number and distribution of constituent droplets delivered to each reservoir. Furthermore, liquid rapidly. Thermal control is enhanced by locating the heating elements proximate to the droplets and reducing the parasitic thermal losses between the heater and the droplet. Heating elements can be integrated into the top plate and/or bottom plate of the droplet microactuator.

Integrating heating elements onto the droplet microactuator also enables the use of multiple distinct thermal zones within the droplet microactuator. This permits multiple steps in an analysis, such as sample preparation and thermal cycling, requiring different temperatures to be performed simultaneously on different portions of the droplet microactuator. Droplets can be physically transported or "shuttled"

between zones of different fixed temperatures to perform the thermal cycling aspects of the amplification reaction. This approach can produce even faster reactions, since heating and cooling of the entire thermal zones is no longer rate-limiting. Instead, heating and cooling rates are determined by the time required to transport the droplets between the zones and the time required for the droplet temperature to equilibrate to the temperature of the zone once it arrives within the zone, both of which are expected to be very fast. A further advantage is that reaction steps can be "queued" rather than "batched" to permit greater operational flexibility. For example, discrete samples can be continuously fed into the droplet microactuator rather being delivered at a single point in time.

Droplets may be thermally cycled in batch mode using a single heater or in flow-through mode by circulating the droplets through distinct temperatures zones created by the one or more heating elements. The essential difference between batch and flow-through modes is that in batch mode thermal control is effected by varying the temperature of the heater while in flow-through mode, thermal cycling is effected by transporting the droplets among distinct constant temperature zones. In the "batch" method, a single integrated thin-film heater on the droplet microactuator can be used to thermally cycle static droplets located within the heater zone. In the "flow-through" method, one or more temperature zones is created on the droplet microactuator and thermal cycling is performed by shuttling the droplets into proximity with or away from the heater or among two or more zones.

In the "batch" case, the thermal mass of the heater itself as well as thermal losses may be minimized through the use of thin-film heaters placed directly adjacent to the droplets. Because the thermal masses, including the droplet itself, are so small, rapid temperature changes can be effected. Passive cooling (in filler fluid) is also rapid because the total energy input into the system is extremely small compared to the total thermal mass.

For "flow-through" heating, a larger thermal mass is sometimes desirable because it helps to stabilize the temperature while a slower ramp rate is tolerable because the heater temperature is not varied once it reaches its set point. A flow-through system can, for example, be implemented using block heaters external to the droplet microactuator which were more accurate and easier to control than thin-film heaters although, in principle either type of heater could be used to implement either method.

In another embodiment, temperature is controlled by flowing or recirculating heated filler fluid through the chip and around the droplets.

The droplet microactuator layout is scalable, such that a droplet microactuator may include a few as one heating zone up to tens, hundreds or more heating zones.

8.3.7.2 Heater Types

Heaters may be formed using thin conductive films. Examples of suitable thin films include Pt heater wires and transparent indium-tin-oxide (ITO). ITO provides better visualization of the droplets for real-time observation. A remotely placed conventional thermocouple (TC) for temperature regulation can also be used. In one embodiment, tiny metal (e.g., copper) vias in the PCB substrate are used to create tight thermal junctions between the liquid and the remote TC. Further, sample temperature can be determined by monitoring the copper via using a surface mount thermistor or an infrared sensor. One advantage of using a thermistor is that they are small enough (2×2 mm) to be soldered directly on the droplet microactuator, while an advantage of using IR is that it is non-contact method which would simplify the interfacing. Because the thermal conductivity of copper is at least 700 times greater than the FR-4 substrate (350-390 W/m·K versus 0.3-0.5 W/m·K) the temperature of a Cu via will accurately represent the temperature inside the liquid. Heaters may be integrated on the bottom and/or top (when present) plate of the droplet microactuator and on the bottom and/or top surface of either plate, or integrated within the structure of either plate.

In one flow-through embodiment, reduced thermal gradients can be provided by using heaters to create a continuous temperature gradient across a region of the droplet microactuator (e.g., from 100 to 50° C.). The use of a continuous gradient will eliminate the need to overcome the steep temperature gradients found along the edge of the heater blocks. A controlled temperature gradient would also significantly enhance the functionality of the device by allowing protocols with arbitrary numbers of temperature points to be implemented. Furthermore, each reaction can be performed with a custom thermal protocol while only the temperatures of the two or more blocks would need to be thermally regulated. The droplets will be transported to and held at the appropriate location between the heaters to achieve a target temperature. The fluorescence of the droplets can be imaged using a fluorescence sensor as they are transported over a detection spot. The temperature of the upper and lower target temperatures can be varied by changing the location of the droplets. Nevertheless, the inventors have surprisingly discovered that thermal cycling, e.g., for PCR, can be readily accomplished using a single heater by transporting the droplet into proximity with and away from the heater.

In some embodiments, heaters located above the droplets may obscure the droplets thus interfering with real-time optical measurements. In such cases, the droplets can be transported out from underneath the heaters to a location which is preferred for optical detection (i.e. a detection spot). Droplets may be periodically transported out from underneath the heaters to a detection spot on the droplet microactuator detection purposes, e.g. detection by fluorescence quantitation. Droplets may be routed into proximity with a sensor while cycling them from one temperature zone to another.

8.3.8 Droplet Operations

The droplet microactuator may conduct various droplet operations with respect to a droplet. Examples include: loading a droplet into the droplet microactuator; dispensing one or more droplets from a source droplet; splitting, separating or dividing a droplet into two or more droplets; transporting a droplet from one location to another in any direction; merging or combining two or more droplets into a single droplet; diluting a droplet; mixing a droplet; agitating a droplet; deforming a droplet; retaining a droplet in position; incubating a droplet; heating a droplet; vaporizing a droplet; cooling a droplet; disposing of a droplet; transporting a droplet out of a droplet microactuator; other droplet operations described herein; and/or any combination of the foregoing.

Droplet dispensing refers to the process of aliquoting a larger volume of fluid into smaller droplets. Dispensing is usefully employed at the fluidic interface, the input reservoirs, and at processing reservoirs. Droplets may be formed by energizing electrodes adjacent to the fluid reservoir causing a "finger" of fluid to be extended from the reservoir. When the fluid front reaches the terminal electrode, the intermediate electrodes are de-energized causing the fluid to retract into the reservoir while leaving a newly-formed droplet on the terminal electrode. As previously noted, one or more electrodes in the reservoir may also be energized to assist in separating the droplet being dispensed from the bulk fluid. Because the droplet conforms to the shape of the electrode, which is fixed, excellent accuracy and precision are obtained. Droplet dispensing is controlled by the controller. In some embodiments the invention employs droplet dispensing structures and/or techniques described in U.S. Pat. No. 6,911,132, entitled "Apparatus for Manipulating Droplets by Electrowetting-Based Techniques," issued on Jun. 28, 2005 to Pamula et al.; U.S. patent application Ser. No. 11/343,284, entitled "Apparatuses and Methods for Manipulating Droplets on a Printed Circuit Board," filed on filed on Jan. 30, 2006; U.S. Pat. No. 6,773,566, entitled "Electrostatic Actuators for Microfluidics and Methods for Using Same," issued on Aug. 10, 2004 and U.S. Pat. No. 6,565,727, entitled "Actuators for Microfluidics Without Moving Parts," issued on Jan. 24, 2000, both to Shenderov et al., the disclosures of which are incorporated herein by reference.

In some embodiments, droplet operations are mediated by electrowetting techniques. In other embodiments, droplet operations are mediated by electrophoresis techniques. In still other embodiments, droplet operations are mediated by electrowetting techniques and by electrophoresis techniques.

In one embodiment, separations may be performed using a combination of electrowetting and electrophoresis. Electrowetting microactuation can be used to create a channel to perform electrophoresis; to deliver a sample to the channel or capture a sample fraction from channel following an electrophoretic separation. For example, for forming a channel, electrowetting can be used to deform (stretch) a droplet of separation medium in a long thin shape followed. In some cases, the channel may be polymerized, e.g., using UV polymerization. In other cases, the channel may be formed by using droplet operations to add droplets into a physically confined microchannel. In a related embodiment, the effective length of an electrophoresis channel can be increased by capturing the fraction of interest in a droplet at the output and then returning it to the input in a cyclical fashion. Using the same principle, a series of progressively finer separation can be performed. Separations may also be accomplished using multiple different separation mediums at the same time.

Droplet splitting or dividing of droplets generally involves separating a droplet into two or more sub-droplets. In some cases, the resulting droplets are relatively equal in size.

Transporting involves moving a droplet from one location to another in any direction. Droplets may be transported on a plane or in three dimensions. It will be appreciated that a variety of droplet operations, such as dispensing and/or splitting may include a transporting element, in which on droplet is transported away from another droplet.

Merging involves combining two or more droplets into a single droplet. In some cases, droplets of relatively equal size are merged into each other. In other cases, a droplet may be merged into a larger droplet, e.g., combining droplet with a larger volume present in a reservoir.

Mixing a droplet involves various droplet manipulations, such as transporting or agitating, that result in a more homogenous distribution of components within the droplet. In one mixing embodiment, a droplet positioned over an electrowetting electrode is rapidly and cyclically deformed in place by activating and deactivating the electrode, inducing fluid currents within the droplet which facilitate mixing. Frequency-dependent effects such as mechanical resonances may be used to tune the quality and speed of mixing. Compared to techniques which require transport of droplets on a surface for mixing this approach minimizes the area required for mixing. This mixing scheme can be employed without the presence of a top plate. Due to space-saving advantage, this scheme could provide for simplified mixing in reaction wells since only one electrode is needed.

Reagents or samples from reservoirs may be dispensed as discrete droplets for transport to other locations on the droplet microactuator.

The invention can include droplet operations using droplets comprising beads. A variety of such operations are described elsewhere herein. In one embodiment, beads are used to conduct droplet operations on reagents that are prone to interfere with droplet operations. For example, certain proteins may be prone to bind to surfaces of a droplet microactuator and/or to partition into the filler fluid. Immobilizing such compounds on hydrophilic beads can be used to facilitate droplet operations using the compounds. The compounds can be bound to the beads, and the beads can contained with a droplet which is subjected to droplet operations.

In one particular dispensing operation, coagulation is used to separate serum from whole blood. Whole blood is loaded onto the chip and combined with a droplet comprising a coagulating agent. Following coagulation, droplets are dispensed from the sample. Because cells and platelets are trapped in place, the liquid dispensed from the sample will contain only serum.

8.4 Kit

A further aspect of the invention is a kit including reagents, sample collection devices, and/or a droplet microactuator or cartridge for conducting the methods of the invention.

9 CONCLUDING REMARKS

The foregoing detailed description of embodiments refers to the accompanying drawings, which illustrate specific embodiments of the invention. Other embodiments having different structures and operations do not depart from the scope of the present invention.

This specification is divided into sections for the convenience of the reader only. Headings should not be construed as limiting of the scope of the invention.

It will be understood that various details of the present invention may be changed without departing from the scope of the present invention. Furthermore, the foregoing description is for the purpose of illustration only, and not for the purpose of limitation, as the present invention is defined by the claims as set forth hereinafter.

We claim:

1. A sample analyzer comprising:
  (a) an analyzer unit comprising:
    (i) electronic or optical receiving means;
    (ii) a means of electrical interface between the cartridge and the analyzer, wherein electrical signals may pass between the cartridge and analyzer unit;
    (iii) a control module which provides instructions to one or more of the following:
      (1) means for converting bulk liquid sample into discrete droplets of known volume;
      (2) means for transporting the droplets;
      (3) means for preparing sample droplets for analysis;
      (4) means for converting one or more stored reagents into discrete droplets;
      (5) means of combining and/or mixing sample and reagent droplets to perform an assay; and
      (6) an assay sensor module housed in the cartridge, wherein the means for transporting droplets delivers the raw or prepared sample to the sensor module;
    (iv) a means for storing one or more reagents, wherein reagent storage comprises one or more sealed pouches, each pouch comprising a required reagent wherein the one or more sealed pouches are mechanically or electrically pierceable to allow flow onto a chip surface, and wherein controlled volume delivery of the reagent is accomplished using droplet actuation, and wherein the means for storing one or more reagents is controlled by the control module;

(v) a means for locally storing the data from detectors and other subsystems;

(vi) a detector module comprising at least one optical detector positioned to correspond to the cartridge optical signal;

(vii) a means of interpreting data from electronic detectors and/or optical detectors;

(viii) a means of displaying test results and other messages;

(ix) a communication module adapted to communicate with a user;

(x) a means for accepting user input; and (b) a cartridge comprising self-contained droplet handling capabilities, wherein the cartridge is coupled to the analyzer unit by a means which aligns electronic and/or optical outputs from the cartridge with electronic or optical receiving means on the analyzer unit.

2. The sample analyzer of claim 1 wherein the cartridge does not comprise a pressure source or vacuum source external to the cartridge.

3. The sample analyzer of claim 1 wherein the analyzer is a portable device.

4. The sample analyzer of claim 1 wherein the analyzer is a handheld device.

5. The sample analyzer of claim 1 wherein the analyzer unit provides analysis for one of the following: a blood chemistry, hematology, immuno-diagnostics, tests for drugs of abuse, serum cholesterol, glucose, FOBT, pregnancy, ovulation, DNA based assays, immuno assays, proteomics, DNA sequencing, and genomics.

6. The sample analyzer of claim 1 wherein the cartridge comprises one or more pressure seals sealing one or more reagents.

7. The sample analyzer of claim 6 wherein the one or more pressure seals are arranged to be broken when the analyzer is coupled to the cartridge.

8. The sample analyzer of claim 1 further comprising a communication module including one or more of the following components: a processor, a display, a radio frequency chip, an antenna, memory containing an operating system, RAM, DRAM or a PCMIA interface, a printer, a network, or computer.

9. The sample analyzer of claim 8 wherein the communication module includes a transmitter and a receiver, both in communication with an information management system, wherein the information management system is a centralized means for collecting and processing information for functions.

10. The sample analyzer of claim 8 wherein the communication module includes a transmitter.

11. The sample analyzer of claim 10 wherein the transmitter is adapted to one or more interfaces selected from the group consisting of radio frequency, infrared and standard ports.

12. The sample analyzer of claim 10 wherein the transmitter is adapted to communicate with a remote database.

13. The sample analyzer of claim 8 further comprising a means for acquiring historical data locally via the communication module.

14. The sample analyzer of claim 13 further comprising a means for storing historical data locally in association with the communication module, the analytical detector module, the cartridge or the assay sensor module.

15. The sample analyzer of claim 1 further comprising a means for storing the information locally in an information storage unit associated with the analyzer.

16. The sample analyzer of claim 1 wherein the analyzer further comprises a plurality of assay sensors, each of the sensors performing the same analysis on a biological fluid.

17. The sample analyzer of claim 1 wherein the analyzer further comprises a plurality of assay sensors, and two or more of the sensors perform different analyses on a biological fluid.

18. The sample analyzer of claim 1 wherein more than one sample from a single test subject or more than one sample from multiple test subjects may be collected, loaded onto a single cartridge, and analyzed by the system.

19. The sample analyzer of claim 1 wherein the means for accepting user input is selected from the group consisting of buttons, touch screen, voice commands.

20. The sample analyzer of claim 1 wherein the cartridge includes a plurality of assay sensors, each of the sensors performing the same analysis on the sample.

21. The sample analyzer of claim 1 wherein the cartridge includes a plurality of assay sensors including at least two sets of one or more sensors, wherein each set performs a different analysis on the sample.

22. The sample analyzer of claim 1 wherein the cartridge includes no electrical sensors and electrical assay detection is performed by electric sensing means mounted on the analyzer.

23. The sample analyzer of claim 1 wherein the cartridge includes no optical sensors and optical assay detection is performed by optical sensing means mounted on the analyzer.

24. The sample analyzer of claim 1 programmed and configured to display historical data locally on the display.

25. The sample analyzer of claim 1 further comprising a means for transferring information, wherein the transferring of information is accomplished via an information management system.

26. The sample analyzer of claim 1 further comprising a means for processing information, wherein the processing of information is accomplished via an information management system that includes procedures for brokering medical data.

27. The sample analyzer of claim 1 further comprising a means for processing information, wherein the processing of information is accomplished via an information management system that includes patient management procedures.

28. The sample analyzer of claim 1 further comprising a means for processing information, wherein the processing of information is accomplished via an information management system that includes procedures for administering the medical analysis.

29. The sample analyzer of claim 1 wherein the cartridge houses a calibrating liquid control, wherein the assay or assays are performed on the calibrating liquid control prior to, after, or simultaneously with the assays themselves.

30. The sample analyzer of claim 1 wherein feedback between the detector module and control module occurs such that once adequate results are captured by the detector module the test can be terminated.

31. The sample analyzer of claim 1 wherein converting bulk liquid sample into discrete droplets of known volume comprises electrowetting mediated droplet operations.

32. The sample analyzer of claim 1 wherein transporting the droplets comprises electrowetting mediated droplet operations.

33. The sample analyzer of claim 1 wherein converting one or more stored reagents into discrete droplets comprises electrowetting mediated droplet operations.

34. The sample analyzer of claim 1 wherein combining and/or mixing sample and reagent droplets comprises electrowetting mediated droplet operations.

35. The sample analyzer of claim 1 wherein droplet handling comprises electrowetting mediated droplet operations controlled by the analyzer unit.

* * * * *